(12) United States Patent
Lee

(10) Patent No.: US 7,005,146 B2
(45) Date of Patent: Feb. 28, 2006

(54) COMPLEX PRESCRIPTION OF CHINESE MEDICINE FOR THE TREATMENT OF EXTENSIVE CANCER

(76) Inventor: Chien-Yung Lee, 2F, No. 60, Shouhua Rd., Gangshan Jen, Kaohsiung Hsien (TW)

( * ) Notice: Subject to any disclaimer, the term of this patent is extended or adjusted under 35 U.S.C. 154(b) by 417 days.

(21) Appl. No.: 10/457,457

(22) Filed: Jun. 10, 2003

(65) Prior Publication Data

US 2004/0219226 A1 Nov. 4, 2004

(30) Foreign Application Priority Data

Apr. 23, 2003 (CN) ........................................ 03122989 A

(51) Int. Cl.
*A61K 35/78* (2006.01)

(52) U.S. Cl. ..................................................... 424/725
(58) Field of Classification Search .................. 424/725
See application file for complete search history.

Primary Examiner—Michael Meller
(74) Attorney, Agent, or Firm—Browdy and Neimark, P.L.L.C.

(57) ABSTRACT

A complex prescription of Chinese medicine for the treatment of extensive cancer, or cancer of relation type of the lymph node. The ingredients of this complex prescription are Pilose asiabell root, Astragalus root, Coix seed, Eupatorium, Tangerine peel, Justicia, Prunella spike, Serissa serissoides, Capejasmine fruit, Forsythia fruit, Red peony root, Rhubarb, Blister beetle, Oldenlandia, Polygonum perfoliatum, Subprostrate sophora root, Shrubalthea bark, Rhizome of arisaema, Chinese Lobelia, Ampelopsis, Globethistle, Pyrrosia leaf, Frankincense, Myrrh, Paris chinensis franch, Patrinia, Dahurian angelica root, Belamcanda rhizome, Dandelion herb, Lemmaphyllum microphyllum, Gleditsia spine, Pubescent angelica root, Chinese Ephedra, and Cimicifuga rhizome. The extraction is improved and it also adopts Indian Bread (Poria), an effective cancer medicine, as excipient.

2 Claims, No Drawings

COMPLEX PRESCRIPTION OF CHINESE MEDICINE FOR THE TREATMENT OF EXTENSIVE CANCER

BACKGROUND OF THE INVENTION

1. Field of the Invention

This invention concerns a complex prescription of Chinese medicine for the treatment of extensive cancer 2. Description of the Related Art The medicine for the treatment of cancers with certain effect has still not been found in the market or even in production. The treatment of cancer is in the slough of anticancer. While the treatment against, destroying or exterminating cancer is still doubtful, the temporary treatment of vascular thrombembolia, radiotherapy or chemotherapy of the intravenous drip is taken as normal treatment. As it ignores the holistic pathology of the victim due to its aboriginality, the treatment effect is still very primal. When the course of treatment is harsh and complicate, the patient will suffer a lot, especially when the patient has dosage dependence, allergic reaction, enhance transfer, etc.

As troubled by the business interest and many other factors, the research of cancer treatment has been confined in a certain mode. The idea that anticancer is the treatment of cancer has been highly advocated; however, the most attractive theory, before it reaches its objective, is still a presumption. The presumptive theory which cannot reach its objective finally certainly has some inherent problems. Therefore it is urgent to break up the mindset of treatment. Before we can find the treatment finally, all the presumptive theories without sound medical foundation are mirages.

If the experts who only know biotechnology and development of cancer medicine have no clinic experience in the treatment of cancer or they only know cancer cells but not know cancer environment or cancer development, etc, they can only develop anticancerous medicine, far away from the practice of cancer treatment.

The researches of cancer structure, organization, shape, and position are equally important. We used to classify the cancers as per those mentioned elements or organic systems; however, as per the practice of cancer treatment, this classification method is unrealistic; therefore the classification by mechanism and type is feasible.

China is noted for its richness of Chinese medicine resource. It has achieve considerably success in anticancer and treatment of cancer over years with many relevant papers released; however most of the treatments are centered around medicines and their production and except the discussion of diagnosis and treatment based on an overall analysis of the illness and the patient's condition, they cannot break away the idea that anticancer is the treatment of cancer. Therefore no innovation or new theory has been brought about. Besides, there is no exact description of the terminology. It is understandable that there is no production scale.

SUMMARY OF THE INVENTION

The invention objective is provide a complex prescription of Chinese medicine for the treatment of extensive cancer and the relevant new ideas, new theories, and new references. The new treatment concerning changeable cancer environment will destroy the old mode against, destroying or extinguishing cancer cells to develop a new way in the treatment of cancer through traditional Chinese medicine.

Another objective is providing the corresponding compound ingredients and prepared method. Besides, the simple oral administration will raise the effect of cancer treatment and lower the medical expense, a real step benefiting the cancer patients.

To fulfill the above-mentioned objectives, we are going to provide the relevant works and attachments and will discuss the new theory, treatment category, type and mechanism, medicine formulation, clinical experiment, effective statistics, and statistics of the cancerous transfer as follows:

DETAILED DESCRIPTION OF THE INVENTION

The old practice on the idea of anticancer cannot break away the bottleneck and raise the effectiveness; therefore the inventor invented a new treatment method—changeable cancer environment. As the application, improvement and test of this method have been carried out over years, it has reached its original projected objective. However this treatment method came from the new theory of consistency of the inventor. For your better understanding, I would like to tell you more about it.

The foundation of this new theory is the theory of birth, grown-up, ageing and death, the theory of barter material change for environment, the theory of cyclic pathology, the theory of six essential factors for the cancerous pathology and undertake the treatment and the theory of cancer transfer in the mechanism. This new theory is an innovation from the traditional Chinese medicine, as it employs philosophic ideas such as the ideas from Lao Zi (Li Dan) (about BC 580). According to the physical phenomena and rules, I hereby bring about the theory on cancer treatment.

First of all, the theory of birth, grown-up, ageing and death (please refer to the first part of Chapter Two of New Road to Development of Therapy in the $21^{st}$ Century copyright No.5-578-235, USA) concerns that the object which can multiply its offspring is self-emerging object, or living object. The living object cannot live forever. It will have to experience the stages of birth, grown-up, ageing and death; therefore the cancer cells will disappear naturally itself.

Therefore it is necessary to understand the situation of birth, grown-up, ageing and death of cancer cells, especially the changeable process and cause in the patient environment; and then understand the theory of barter material change for environment (please refer to the second part of Chapter Two of New Road to Development of Therapy in the $21^{st}$ Century copyright No.5-578-235, USA). In this theory, we can find a common property in the survival of living object: the survival of living object, in the relation with category, class, family, and genus, has its certain environment adaptation, which is related to birth, grown-up, ageing and death of the living object closely. In the cozy environment, the living object will grow prosperously, while in harsh environment, it will be ageing very fast. In this theory, there are other precious discoveries: the forming of environment can be decided by the property of added materials. For example, in the normal environment of the human body, which is not an ideal environment for the growth of cancer cells, when the unusual material is added in, because they change the original environment, they create an ideal environment for the growth of the cancer cells, which is the mechanism of cancer suffering.

Fortunately, medicine is kind of object. Especially the traditional Chinese medicine with over 8000 categories, from the traditional record and modern research, is typical object possessing the quality of flavor, taste, ingredients, and comprehensive medical function. If we can understand the practical situation of the cancer environment and can choose suitable medicine, with careful configuration and taking method, we can form another environment with the help from the medicine, an environment which is disagreeable with the growth of the cancer cells. Therefore, the cancer can be cured.

The environment which is agreeable with the growth of cancer cells is obviously different to the normal environment. It is called as special cancer environment. Through clinic experiment and research, we have to understand its pathologic phenomena, which concerns the theory of the pathology of the cyclic environment (please refer to Chapter Four and its attachment of New Road to Development of Therapy in the 21$^{st}$ Century copyright No.5-578-235, USA), which exists in all the cancer patients. Its external behaviors are as follows: (1) hypofunction of pancreas, and bad links with other organs; (2) exchange obstruction in the liver, portvein and spleen with hyperbaric symptom; (3) the hypofunction and obstruction of the defense tissue and lymphokinesis. These three environments are three cozy environments for the cancer cells.

All the living objects have six elements: power, space, substance, humidity, airflow, temperature. The human body is under this rule too. (please refer to Chapter Five of Part I of the Key and Lock of Chinese Medicine copyright NO.2003-A-0685, mainland). No one can be deprived of one element; otherwise he will die. These six elements should have certain cooperation. Any abnormal cooperation will lead to sickness. The finest part of research and treatment of cancer is that we can understand the change and abnormality of these six elements in the cancer environment and then apply certain treatments, which is the pathology and treatment of cancer through six elements (please refer to Chapter Seven of Part II of the Key and Lock of Chinese Medicine copyright NO.2003-A-0685, mainland).

There are many classification methods as per the organization, structure, physical condition, position or system of the cancer. To have an effective treatment, the inventor had a deep research of the relation among the different cancers. As per the mechanism, there are basically three types (please refer to the following part). Cancers transfer and diffusion are both important and have very close relation with the chemotherapy and radiotherapy treatment, but lack of such records and theories before. We can know the new theory "Cancers Transfer" and reasons of transfer and diffusion from this type mechanism certified by dynamic statistics of cancer species.

Cancer belongs to the epithelial tumor and it mainly occurs in the skin(face, head, limb and etc.), mucosa(oral cavity, esophagus, stomach, intestines, uterus and etc.), gland and viscera(mamma, liver, kidney, lung and etc.). The cancer doesn't primary appear in the nonepithelial bone, muscles, connective tissue, nervous tissue and etc. According to tissue species, it can be divided into: 1. epidermoid carcinoma or squamous cell carcinoma. 2. simple carcinoma or adenocarcinoma or cuboidal cell carcinoma. 3. adenocarcinoma or cylindrical cell carcinoma. 4. colloid carcinoma or mucoid carcinoma. According to clinical characters, it also can be divided into: 1. dermal cancer (skin cancer), including skin squamous cell carcinoma, deep-in cancer and papillary carcinoma. It frequently occurs in face, head, neck, chest, umbilicus, vulva, limb and etc. 2. mucosa cancer, including epithelial mucosa, tubular epithelial-mucosa which the former frequently occurs in lip, oral cavity, maxillary sinus, esophagus, vagina, penis and etc., while the later frequently occurs in stomach, intestine, gallbladder and etc. 3. substance organ-cancer, frequently occurs in mamma, liver, kidney, pancreas, ovary, uterus, prostate, thyroid, testicle, and etc.

Cancer researchers shall know all the information of pathologic anatomy, signs-symptoms concerning cancers. But because of the confusion of the guide of "Anti-cancer", shortage of cases and unsatisfactory therapeutic results, it's necessary to reform all the unknown evidences. For example, in most of teaching books in 1950, it showed that status of primary lung cancer is so-called "patients that cancer specially occurs in alveoloepilhelium, bronchial epithelium, bronchopancreatic epithelium are few" and pulmonary cancers mostly are transferred from other cancers. But according to originator's clinical statistics, patients that get pulmonary endothelial cancer are common, while patients that cancer is transferred to other positions mostly have primary condition of lung cancer. In the 17 cases of lung cancer patients of this application, there is 1 patient with primary lung cancer, there are 6 patients with cancers transferred from other positions and there are 5 patients with lung cancer transferring to liver, lymph, bone and keeping symptoms of lung cancer.

According to the special characters of each cancer, differences of nosogenetic elements, relation between cancers of all kinds and etc., cancers are classified based on types and mechanism. Its characteristic rests with the authenticity and efficiency of using drugs. This uses the past therapy drugs for reference which is included in a system, for example: a complex prescription for cancers of digestive system which includes cancers of esophagus, stomach, cardia, liver, pancreas, gallbladder, intestine and etc. But as far as the experience of originator is concerned, there must have obstacles and embarrassment in treating cancers.

Because esophagus, stomach, pylorus and cardia belong to nerve-sensitive position, there must be actions of vomiting, regurgitation and upward invasion as well as symptoms of obstruction and unbearable pain resulted from the inflammation of cancerous protuberance granula. If the urgent symptoms can't be relieved, the drugs can't pass through organs and make its effect. Furthermore, such cancerous protuberance granula has its special characters, then how can use the same drugs with that for cancers of liver and pancreas? Although liver and pancreas are digestive organs, liver is in charge of organs' chemistry, antitoxic task, while internal and external secretions of pancreas is the important task of body. Cancers of liver and pancreas frequently occurs in the inside of organs and therefore they have special characters. Intestine is digestive organ, but according to originator's deep research, there is significant and close relation between intestine and Peyer's Patches and iliac lymph. The pathologic anatomy in 1950 certified: "The species of primary intestine carcinoma except rare porta squamous cell carcinoma are all cylindrical squamous cell carcinoma that occurs in Lieberkulms' glandular epithelium. Most are Adenocarcinoma, then medullary carcinoma, colloid carcinoma, and scirrhous carcinoma."

Thus it can be seen that the close relation between intestine carcinoma and lymph gland and the therapy method of intestine carcinoma can't be mixed with the above-mentioned two therapy methods.

In conclusion, cancers can be classified into three kinds based on the type and mechanism of cancers: 1. allergy type of the upper digestive tract. 2. principle type in liver and gland. 3. relation type of the lymph node, that is the extensive cancer in this application. Such classification will do good to the using and efficiency of drugs.

Primary cancers or cancers transferring to different organs and tissues have its different name. In order to make therapy strategy, make using drugs convenient and efficient, its' necessary to discuss, research each etiopathogenesis and pathology one by one. The classification is based on the difference and relation of etiopathogenesis and pathology of each type. It can make full use of drugs and improve their efficiency if doctors treat patient with different drugs according to actual status and cancer type.

The cancers are classified as three types by the originator based on this principle: 1. allergy type of the upper digestive tract. 2. principle type in liver and gland. 3. relation type of the lymph node. "Extensive" in this application means the relation type of the lymph node which includes many cancers. The definition of "relation type of the lymph node" means all cancer species concerning this type are directly and close related with lymph node and lymphatic system. Now explain the mechanism of this type as follows:

Cancers of thoracic cavity, head, neck and etc., are close related with the lymph node of maxillary sinus, throat, tongue, tonsil, chin, neck, clavicle, thymus and pulmonary gland, axilla and etc. The above-mentioned lymphs are very close so that their functions can be influenced each other and the probability of primary cancers transferring level and transferring each other is high. The circulations of such lymph are all transferred to blood circulation from subclavian vein angle and shortage of lower lymphatic vessels, therefore the probability for cancers at upper part of body transferring down is much lower under the normal standings.

Cancers at the lower part of body such as cancers of lower abdominal cavity, kidney, bone and etc., are close related with lymphatic node of cisterna chyli, ilium, Peyer's patches, groin, and etc., and neighboring lymphatic systems. Such lymphatic nodes are very close with each other so that they can influence function directly and the probability of primary cancer transferring level and transferring each other is high. But there are net-micro-lymph-vessels near the organs of lower abdominal cavity. When such vessels gather gradually, they join the cisterna chyli: that is to move up along lymphatic vessels. Before they infuse into subclavian veins, cancerous cells move up along lymph and meet with lymphatic node. When the function of lymphatic node can't meet with this mission, it will form the mechanism of inferior cavity cancers transferring up and therefore, the probability of inferior cavity cancers transferring up is very high. Cancers transferring to liver is resulted from portal vein.

Probability of cancers transferring lever and transferring in the same position resulted from the above-mentioned reasons is high, and probability of inferior cavity cancers transferring up is high while probability of superior cavity cancers transferring down is low. But in fact, there are some the upper center cancers transferring down. Statistics find out that the abnormal phenomena are resulted from the chemotherapy and radiotherapy treatment. When the superior cavity, head, neck, chest and breast accept drastic chemotherapy and radiotherapy treatment, the organs and tissues of the body can't escape from this torture because of their adhesive materials, while the killing and free cancerous cells can get rid of this misfortune as they have many places to hide. Such cancerous cells have the natural instincts of choosing comfortable circumstances, therefore, when they jump into radical environment changes, they may escape to the farthest place-hypogastric cavity (abdomen cavity) and mostly choose buttocks, leg and lumbar vertebra that lack of lymphatic vessels. This is the mechanism of most cancers transferring down when accepting chemotherapy and radiotherapy treatment.

Statistics conclude as follows: A. the ability of the upper center cancers (superior cavity and head) transferring down is very low, and much lower than that of transferring lever and up. B. the ability of transfer of the upper center cancers with the chemotherapy and radiotherapy treatment can be raised 4.5 times, while that of transferring down can be raised 15.5 times. C. The lower center cancers transferring up without the chemotherapy and radiotherapy treatment is 8 times of the upper center cancers transferring down. Because the lower center cancers has the high ability of transferring up, there's less influence for transferring up with the chemotherapy and radiotherapy treatment. (please read "Statistics of Cancers Transfer" for reference)

The result of the above statistics is enough to certify that the extensive cancers of "relation type of the lymph node" not only have close relation, but also have direct influence towards their functions and work. Abiding by the sound strategy, choose sound drugs and make full of the pharmacological effect of drugs' severalty and combination. That is to say: let drugs change the abnormal environments of lymphatic nodes of inferior/superior cavity and lymph circulation, and actuate the cancerous cells to have "Sick" feeling. The above result is one of the important reasons for this application.

A complex prescription of Chinese medicine for the treating extensive cancers consists of the following concentrated and extracted drug powder according to the specified ratio. Fuling (Indian Bread) of 1 is the powder of the extracting excipient, and its ingredient and content are all included in each drug.

| | |
|---|---|
| 1. | Fuling (Indian Bread) |
| 2. | Dangshen (Pilose Asiabell Root) |
| 3. | Huanggi (*Astragalus* Root) |
| 4. | Yiyiren (*Coix* seed) |
| 5. | Shanpeilan (*Eupatorium*) |
| 6. | Chenpi (*Tangerine* peel) |
| 7. | Juechuang (*Justicia*) |
| 8. | Xiakucao (*Prunella* spike) |
| 9. | Liangfencao (*Serissa serissoides*) |
| 10. | Zhizi (Capejasmine fruit) |
| 11. | Liangiao (*Forsythia* fruit) |
| 12. | Chishao (Red peony root) |
| 13. | Dahuang (*Rhubarb*) |
| 14. | Zhechong (Blister beetle) |
| 15. | Bai Huashe-shecao (*Oldenlandia*) |
| 16. | Gangbanggui (*Polygonum perfoliatum*) |
| 17. | Shandougen (*Subprostrate sophora* root) |
| 18. | Mujinpi (Shrubalthea bark) |

-continued

| | |
|---|---|
| 19. | Tiannanxing (Rhizome of arisaema) |
| 20. | Banbianlian (Chinese Lobelia) |
| 21. | Bailan (*Ampelopsis*) |
| 22. | Loulu (Globethistle) |
| 23. | Shiwei (*Pyrrosia* leaf) |
| 24. | Ruxiang (Frankincense) |
| 25. | Moyao (Myrrh) |
| 26. | Zao xiu (*Paris chinensis* franch) |
| 27. | Baijiang (*Patrinia*) |
| 28. | Baizhi (*Dahurian angelica* root) |
| 29. | Shegan (*Belamcanda rhizome*) |
| 30. | Pugongying (*Dandelion* herb) |
| 31. | Luoyancao (*Lemmaphyllum microphyllum*) |
| 32. | Zaojia (*Gleditsia spine*) |
| 33. | Duhuo (*Pubescent angelica* root) |
| 34. | Mahuang (Chinese *Ephedra*) |
| 35. | Sheng ma (*Cimicifuga rhizome*) |
| 36. | |

In the above herbs, Fuling (Indian Bread) is the powder of the extracting excipient. The proportion of other herbs is 1.94%–3.94% and can be decided to adopt or not and increase its content or decrease its content according to the actual standings. The best proportion of each herb is 2.941%, total 100%.

The pharmacological illustration of each herb is to improve the three phenomena of "pathology of the periodic return", that is: "enhance pancreas function and maintain links with other organs", "remove the obstruction in the portal vein, liver and spleen, maintain and decrease the portal vein pressure", "improve the defense functions and lymph circulation, increase immunity" as well as the four pharmacology such as "pass through lymphatic node and other necessary effects". But Chinese medicine mostly has the many-sided pharmacodynamic actions. Therefore, the pharmacology may include the above-mentioned effects so that we shall make the expedient prescription and attach the details for explanation.

1. Enhance Pancreas Function and Maintain Links with Other Organs:

Fuling (Indian bread): Replenish nutrition, enhance pancreatic function and immunity, relieve uneasiness of the body and mind, regulate the heart beat and electrolytic metabolism. Modern pharmacology: Enhance the immune function of the control and loaded tumour mouse, increase the phagocytosis of the rhagiocrine cells, have the active effect upon nasopharyngeal carcinoma, stomach carcinoma, cervix carcinoma and etc. In this invention, it's the excipient vehicle in place of corn and wheat and etc. The extracting and concentrated drug liquid of all kinds except those that are not collected and dried, all use pure Fuling as Vehicle in order to enhance the efficiency of treating cancers.

Dangshen (Pilose Asiabell Root): Enhance pancreatic and pulmonic function, replenish nutrition, improve the quality and secretion of gland. Modern pharmacological experiments certify that it can enhance the emergency action and immune function, defer the senility, have the anti-ulcerative action and etc. It has the active effect upon blood, the function of blood producing, cardiovascular, anti-tumor and etc. Decrease fatty degeneration, improve hepatonecrosis, inhibit the forming of hepato-lymph gap and collagen fibril at central veins. In this complex prescription, it can be used for coordinating the relation between the pancreatic gland and each organs.

Huanggi (Astragalus Root): Replenish nutrition and trace elements, enhance physical power, increase the raised energy of lymphatic vessel, regulate autonomic nerve, prevent the abnormal allergy of sweat gland, regulate the electrolytic metabolism, improve the lymphatic constitution, replenish the defence cells' nutrition. Modern pharmacological experiments certify that it has the active effect upon immune system, does help to metabolism of body and cardiovascular system and has the antiviral and anti-cancerous action.

Yiyiren (Coix seed): Replenish nutrition, activate the pancreatic function and improve organs constitution, especially the obstruction of electrolytic metabolism of pancreatic gland. Remove the abnormal material in muscle, joint and aponeurosis; Relieve inflammation and promote pus discharge. Modern pharmacological experiments certify that it can inhibit the contraction of skeletal muscle, decrease blood sugar, reduce fever, anti-inflammation, dilate pulmonary vessels and etc. It can markedly increase the antibody produced by ending blood mononuclear cells of healthy human, enhance the immunity and anti-tumor action.

Shanpeilan (Eupatorium): Stabilize the function of pancreas, stomach and spleen, enhance the resistibility against summer fever and diaphoresis; reduce fever, promote the electrolytic metabolism of local tissue; promote blood circulation; relieve the toxin in body. Modern pharmacological experiments certify that it has the action against cervical squamous cell carcinoma. This complex prescription can enhance the permeability of organs in the inferior abdominal cavity.

Chenpi (Tangerine peel): Regulate the function of pancreas and stomach, relax the nervousness of upper digestive tract, increase the appetite, remove the mucoid material in tissues, relax the allergy of trachea and bronchus. Because it can dilute the dope, it can indirectly promote the electrolytic metabolism of tissues and lymph and micro-circulation of organs.

2. Remove the Penetration and Obstruction in the Portal Vein, Liver and Spleen, Maintain and Decrease the Portal Vein Pressure:

Juechuang (Justicia): Regulate and decrease the body temperature on high side, promote the electrolytic metabolism of tissue, remove the obstruction of abnormal material in liver, help the peristalsis of digestive tract, abirritation and anti-inflammation. Modern clinical researches certify that it can effectively cure malaxia, infection urinary system, tubercular anal fistula and etc. This complex prescription is used for regulating, decreasing portal vein pressure and treating temperature on high side of straight and large intestines and circulation of lymph system.

Xiakucao (Prunella spike): Remove the obstruction of abnormal material in liver blood sinus, portal vein wall and spleen, smooth the circulation of liver, remove the symptom of inflammation and swellen mass. Modern pharmacology has the obvious effect of decreasing blood pressure. Clinical treatment of icteric hepatitis and pulmonary tuberculosis is effective.

Liangfencao (Serissa serissoides): Relieve the malaise and disease of the human body caused by the summer fever, increase the Yin element in blood, remove the radical component of human body, clean away the toxic materials, quench thirst, clean away heat and diminish inflammation. It can treat hypertension, diabetes, the pain in bone resulted from the infection of venereal disease. This complex prescription is used for regulating, decreasing portal vein pressure, treating temperature on high side of cancer environment and removing the radical toxins.

Zhizi (Capejasmine fruit): Remove the radical element in blood, regulate and decrease the temperature on high side, promote the electrolytic metabolism of body, clear away heat, benefit gallbladder, remove heat toxin, regulate and decrease the portal hypertension, smooth the hepatic circulation, remove the inflamed environment of cancers.

Liangiao (Forsythia fruit): Clear away the heat, subdue inflammation, remove the toxin, induce diuresis, open and through the lymph, remove the swollen mass of lymph node. Modern pharmacological experiments certify that Liangiao has a broad-spectrum anti-organism action, subdues inflammation, has the effect against hepatic injury, enhances the strength and tenacity of terminal vessel and prevents bleeding. This complex prescription is used for antihypertensive of giving the cool and improving change cancerous environment.

Chishao (Red peony root): Clear away heat, regulate and decrease the blood temperature, remove the thrombus, promote the blood circulation. Modern pharmacological experiments certify that it can subdue the thrombus forming, against the platelet agglutination, decrease the blood lipid and restrain the atherosclerosis against the tumor, nourish the liver, improve the blood circulation action.

Dahuang (Rhubarb): Nourish the liver, benefit the gallbladder, against the gastic and duodenal ulcer, prevent the absorption of water in the colon, quicken the removing of substance, induce diarrhea action, have the anti-bacterial, anti-viral, anti-fungal action. When removing the toxic material in body, it can relieve the high pressure of portal vein.

Zhechong (Blister beetle): Have anit-coagulant action, remove the thrombus in the blood vessel, smooth the circulation of screw artery, micro-blood vessel, relieve the thrombus, remove the dead cancerous cells or toxic materials combined with other drug therapy.

3. Improve Defense Function and Lymph Circulation, Enhance the Immunity:

Bai Huashe-shecao (Oldenlandia): Clear away the temperature on high side resulted from the radical elements, relieve toxin, promote the circulation of electrolytic metabolism of local tissues and specially the organs in lower abdominal cavity. Modern pharmacological experiments certify that it can enhance the white corpuscles engulf function, increase the immunize function, anti-bacterial and anti-tumor actions, do good to gastric carcinoma and carcinoma of the rectum.

Gangbanggui (Polygonum perfoliatum): Promote the electrolytic metabolism of body, induce diuresis, relieve swollen, reduce fever, clear away thrombus and toxin in tissues. It is used in treating gonorrhea, venereal infective disease and ascites diseases. Modern pharmacological experiments certify that it has the anti-bacterial, anti-viral and anti-tumor actions.

Shandougen (Subprostrate sophora root): Clear away the radical elements of body (bring down the fever), neutralize toxic elements (remove the toxic material), alleviate the laryngeal inflammation and edema, ease pain, kill the intestinal parasites. Modern pharmacology: contain alkaloids of all kinds and have the anti-tumor action.

Mujinpi (Shrubalthea bark): Regulate and decrease the temperature on high side in lung and large intestine, dilute the mucus in tissue, anti-bacterial, kill parasites, have effect upon the treatment of abscess of lung (lung tumor). Modern pharmacology tells us that the erythrotriol of monomer compounds of 7 kinds divided from Mujinpi can inhibit the action of the tumor cells' reproduction.

Tiannanxing (Rhizome of arisaema): Eliminate the initiative pathogenic factors of blood vessel and micrangium pressure, allay excitement, relieve muscular spasm, clear sputum, dilute the mucus in tissue, open and through lymphatic tissue. Modern pharmacological experiments certify that it can have the directly killing or inhibitive action for cancers of lung, liver, stomach, uterus and etc.

Banbianlian (Chinese Lobelia): Regulate and decrease the temperature on high side in the tissue, start the defence organs, promote the function of relieving toxin, enhance the electrolytic metabolism, eliminate ascites and swelling of foot and leg, smooth the lymph metabolism, neutralize the toxin material. Modern pharmacology: diuresis, against snake venom and etc. it can treat ascites of hepatocirrhosis and carcinoma of many kinds.

Bailian (Ampelopsis): Regulate and decrease the abnormal temperature on high side, promote the toxic action of the lymph node and other defense systems, relax the tightening state of ligament of organs and connective tissues, quicken the healing of tissue ulcer. Modern pharmacological experiments certify that it has the anti-bacterial action. The Bailian described by Li Guangxun in 1992 and experiments certify that it has inhibitive action of cervix cancerous cells culture of human JTC-26 and therefore it has the anticancer effect.

Loulu (Globethistle): Promote the blood circulation and lactescence of lying-in woman, decrease the temperature on high side of human body, enhance the detoxifcation function of defense system. Modern pharmacological experiments certify that it has the anti-atherogenic, anti-oxidative, nourishing liver and immunization improving actions and etc.

Shiwei (Pyrrosia leaf): Relax the tension of prostata, induce diuresis, relieve and remove the inflammation symtom of bladder, urethra and prostata, treat the bleeding of bladder and urethra, inhibit the action of bacterium and virus of many kinds in the lower abdomen cavity. The mangiferin has the stronger resistance against the Herpes Simple Virus, prevents the replication of virus at cells. It can raise leucocyte amount for the leukopenia status resulted from chemotherapy and radiotherapy. Enhance the effectiveness of phagocytes in body.

Ruxiang (Frankincense): Promote the normal circulation of blood and lymph fluid, improve the function of defense organs. Combined with other drugs, it can remove the thrombus, cancerous cells and other foreign matters.

Moyao (Myrrh): Promote the blood circulation, remove the obstruction of foreign mater in circulation to dredge the obstruction and achieve effect of alleviation. Clear away the abnormal swelling of connective tissue. According to the modern pathology research, it can regulate and decrease blood lipid and cholesterol, prevent the forming action of atherosclerosis, inhibit the forming of the cholesterol of hepatic homogenate.

4. Penetrate Lymphatic Node and Other Necessary Effects:

Zao xiu (Paris chinensis franch): Allay excitement, open and through the lymph organs and defense tissue, remove the foreign matter in it, clear away the inflammation symptoms in the organs, tissues and liver.

Baijiang (Patrinia): Regulate and decrease temperature on high side, promote the anti-toxic function of defense system, clear away the thrombus, pus fluid, as well as tranquilization, antibacterial and antiviral action in modern pathology. The trial report in 1992 issued by Gao Shujuan shows that if pure (100%) patrima is added into the 10mg endotoxin, can decrease toxic activity, with detoxic rate is 8.7%.

Baizhi (Dahurian angelica root): Have the anti-animalcule action, remove the inflammation, reduce fever, remove the pathogenic factors of producing micro-blood vessel's abnormal pressure (eliminate wind), promote the electrolytic metabolism of tissue (dispel dampness), remove the inflammation and swelling of mucous membrane in nasal and pharynx cavity, ease pain, guide the anti-cancer drugs into head and thoracic cavity to make full use of treating cancer and change cancer environment.

Shegan (Belamcanda rhizome): Against the inflammation, reduce fever, remove the sputum, clear away throat pain, remove and dissolve scrofula. Recorded in ancient books, it can treat the lump of liver and pancreas (the mother of malaria, mass located in the upper abdomen) effectively, while in modern medicine, it can relieve inflammation, reduce fever, clear sputum, resist the microbial (Bacillus anthracis, Bacterium diphtheria, typhoid bacillus, human bacillus, tubercle), and influenza virus, etc.

Pugongying (Dandelion herb): Promote the permeability in lymph tissue, clear away the toxic material of body, regulate the temperature on high side, against the inflammation, remove general anasarca. Modern pharmacology explains that it can resist the pathogenic microorganism, resist gastric ulcer, benefit gallbladder, nourish the liver, start the effectiveness of macro-phagocyte and anti-tumer.

Luoyancao (Lemmaphyllum microphyllum): Clear away the radical composition in body, regulate and decrease the temperature on high side, promote the function of electrolytic metabolism, induce diuresis, assist the function of defence, anti-toxin, killing intestinal parasites, Clear away the radical composition in body, regulate and decrease the temperature on high side, promote the function of electrolytic metabolism, induce diuresis, assist the function of defence, anti-toxin, killing intestinal parasites. The ancient books record that it can clear away the swollen lump in the lower abdominal cavity, scrofula and mastocarcinoma and etc.

Zaojia (Gleditsia spine): Dilute the tissue fluid and viscose material in body, clear sputum, relax the spasm of trachea and bronchus, have the action of relieving cough. Make free the passage of nasal cavity, throat and stool-urine, remove the toxin caused by the obstruction of electrolytic metabolism (eliminate damp toxicity), destroy intestinal parasites, anti-bacterium. Modern pharmacology certifies that it can have anti-bacterial and haemolytic action and etc.

Duhuo (Pubescent angelica root): Remove the abnormal pressure of blood vessel and micrangium and the pathogenic factors caused by obstruction of electrolytic metabolism (rheumatic factors), regulate temperature, ease pain, relax spasm. Modern pharmacological experiments certify that it can have the anti-arrhythmic action, prolong the time of thrombus forming, ease the pain, relax spasm, relieve inflammation and have the anti-bacterial action. The furanocoumarins composition can inhibit the P from incorporating HeLa cells (cervix cancer cells) and kill and destroy the A's ascitic cancer cells.

Mahuang (Chinese Ephedra): Excite the central nervous system, increase the transmitting function of nerves and muscles, deepen the drugs into tissue. It's the necessary drug for lung cancer, lymph cancer and osteosarcoma.

Sheng ma (Cimicifuga rhizome): Increase the raising kinetic energy of lymph fluid at lymph vessels, increase the activity of lymph cells, induce the lymph cells to produce interferon, produce the special actions at the lymph nodes of enteric aggregate nodules (Peyer's patches) and lymph nodes at thymus. It is not the anti-cancer drug, but the guiding drug for treating intestine cancer, lung cancer, head part cancer and etc.

(The brief information of a single drug in the complex prescriptions of Chinese medicine)

| No: 1 | | |
|---|---|---|
| Name of Chinese herbs | Scientific Name/ Fuling Another Name | Indian Bread, Poria Cocos (schw.) WOLF Tuckahoe |
| Basis | Page 1596 of Great dictionary of Chinese medicine, Page 554 Volume 1 of China Ben Cao (Shanghai Science and Technology Publishing House, China) | |
| Source, Collect Season, Segment of the plant | Hubei, Anhui. Ripe after 8–10 months of planting. When the exoderm of sclerotium is becomes brown, it then can be reaped. Dig them out, clear away mud, pile them indoor with straw covered in order to make them sweat (moisture), get rid of scarfskin when the surface becomes crimped and then dry them. | |
| Processing, Extracting process, Method | (1) Select crude drug that is weighty, strong, exodermis brown, peel-grain fine, no crevice, section is white and fine and smooth, adhesion strong to tooth. The method is to raze out coat, infuse to soften, slice up and dry. (2) 50 Kg crude drugs grind throughout 120 mesh sieve, then put fine powder in storage. | |
| Active principle | Sclerotium contains β-Pachyman with the weight approximately 93% of the total dry weight and three compounds-Pachymicacid, 3β-Hydroxylanosta-7.9(11), 24-trien-21-oil acid as well as gum, chitin, fat, sterol, lecithin, glucose, adenine, histidine, choline, fat and protein and etc. decomposed fromβ-pachyman, and 0.23% Ash including Fe, Ca, Mg, K, Na, Ce, P and etc. | |
| Pharmacological action of original record | Replenish nutrition, enhance pancreatic function and immunity, relieve uneasiness of the body and mind, regulate the heart beat and electrolytic metabolism, induce diuresis. Enhance the immune function of the control and loaded tumour mouse, increase the phagocytosis of the rhagiocrine cells, have the active effect upon nasopharyngeal carcinoma, stomach carcinoma, cervix carcinoma and etc. | |
| Application of pharmacology and goal | Replenish nutrition, enhance pancreatic function, immunity and electrolytic metabolism. In this patent, it is mainly used as "Vehicle". The extracted and concentrated drugs of all kinds except those that the raw drugs aren't treated and dried, use pure Fuling as Vehicle in place of the generally used edible amylum such as corn, wheat and etc. | |

| No: 2 | | |
|---|---|---|
| Name of Chinese herbs | Scientific Name/ Dangshen Another Name | Codonopsis, Pilosula, Pilose Asiabell Root, Pilosula (Franch) Nannf |
| Basis | Page 1837 of Great dictionary of Chinese medicine, Page 607 Volume 7 of China Ben Cao (Shanghai Science and Technology Publishing House, China) | |
| Source, Collect Season, Segment of the plant | Shanxi, Henan. Dig out and clear the root after 9–10 months of planting. Put them under the sun for 4–6 h, bind them with rope, knead them. Treat like this for 3–4 times and then bundle them. | |
| Processing, Extracting process, Method | (1) Take 4 Kg raw materials, wash clean, cut segment, put in pot, add water, infuse 3h. Then heat and decoct drugs, take medicinal liquid 2 times. (2) Heat to evaporate water until 3 L medicinal extract liquid remains, add 1 Kg Poria powder and mix them even. (3) Dry at 65 . (4) Crude drugs grind throughout 80 mesh sieve, then collect fine powder for seal and storage. | |

-continued

| | |
|---|---|
| Active principle | Main content of root is the carbohydrate compound of many kinds such as fructose, inulin and etc. It also contains four alleaoids such as syringin and etc., choline, perlolyrine and amino acids of 17 kinds as well as sterols of 12 kinds such as taraxerol, acides, esters, aldehydes compound such as syringaldehyde, and Fe, Cu, Co, Mn, Zn, Mu, Ni, Sr, Al, V, F and etc. |
| Pharmacological action of original record | Enhance pancreatic and pulmonic function, replenish nutrition, improve the quality and secretion of gland. Modem pharmacological experiments certify that it can enhance the emergency action and immune function, defer the senility, have the anti-ulcerative action and etc. It has the active effect upon blood, the function of blood producing, cardiovascular, anti-tumor and etc. Decrease fatty degeneration, improve hepatonecrosis, inhibit the forming of hepato-lymph gap and collagen fibril at central veins. |
| Application of pharmacology and goal | Enhance pancreatic function, improve the quality and secretion of gland, regulate contact between the pancreatic gland and each organs, replenish soft nutrition and inorganic elements. |

No: 3

| | | | |
|---|---|---|---|
| Name of Chinese herbs | Huanggi | Scientific Name/ Another Name | Astragalus, mongholicus Bge, Milkeveteh (root), Milkvetch Root, Root of Membranous Milkvetch, Root of Mongolian Milkvetch |
| Basis | | | Page 2036 of Great dictionary of Chinese medicine, Page 341 Volume 4 of China Ben Cao (Shanghai Science and Technology Publishing House, China) |
| Source, Collect Season, Segment of the plant | | | Shanxi, Nei Meng Gu. Dig the root out in Autumn. Cut the head, sweep off the mud, half dry under the sun, pile for 2 days, then whole dry at another day, arrange and bundle them. |
| Processing, Extracting process, Method | | | (1) Take Huanggi 6 Kg, wash clean, immerse it in the water to soft, cut thin piece, put in pot to immerse with water for 3 h. Then heat and decoct drugs, take medicinal liquid 2 times.<br>(2) Heat to evaporate water, add 1 Kg pona powder and mix even when it remains 3 L medicinal extract liquid.<br>(5) Dry at 65 .<br>(3) Crude drugs grind throughout 100 mesh sieve, then seal up and put them in storage. |
| Active principle | | | Contain ketones, phenols, esters and polysaccharide composition of many kinds such as astragaloside I, II, IV, soyasaponin I, calycosin-7-O-β-D-glucoside and etc. They all can enhance the immune function. It also contains trace elements of over 20 kinds in which Ca, P, Mg, Fe and etc. has high content. |
| Pharmacological action of original record | | | Replenish nutrition and trace elements, enhance physical power, increase the raised energy of lymphatic vessel, regulate autonomic nerve, prevent the abnormal allergy of sweat gland, induce diuresis, regulate the electrolytic metabolism, improve the lymphatic constitution, replenish the defence cells' Nutrition. Modem pharmacological experiments certify that it has the active effect upon immune system, does help to metabolism of body and cardiovascular system and has the antiviral and anti-cancerous action. |
| Application of pharmacology and goal | | | Regulate pancreatic function, improve the lymphatic constitution, replenish the defence cells' nutrition, increase the raised energy of lymphatic vessel, enhance contact with organs. |

No: 4

| | | | |
|---|---|---|---|
| Name of Chinese herbs | Yiyiren | Scientific Name/ Another Name | Coix Lacyma-Jobi L, Coix Seed, Job's Tears, Seed of Job'3 s Tears |
| Basis | | | Page 2645 of Great dictionary of Chinese medicine, Page 329 Volume 8 of China Ben Cao (Shanghai Science and Technology Publishing House, China) |
| Source, Collect | | | Fujian, Taiwan. Collect fruit and dry under the sun, |

-continued

| | |
|---|---|
| Season, Segment of the plant | shell and get rid of involucrum and seed coat. |
| Processing, Extracting process, Method | (1) Take 6 Kg raw materials and wash clean. Take 1 Kg from the 6 Kg raw materials to dry under the sun and be grinded as fine powder. Another 5 Kg are grinded as powder, then put them in pot, add water to infuse them for 3 h, heat under the temperature limit of 70 for 6 h, then release the liquid by three times.<br>(2) Heat to evaporate water, mix even with Yiyiren fine powder when it remains 3 Kg raw materials.<br>(3) Dry at 65 .<br>(4) Crude drugs grind throughout 120 mesh sieve, then put the fine powder in storage. |
| Active principle | Contain protein 16.2%, fat 4.65%, carbohydrate 79.17%, a few vitamin B1 as well as coixul, coixenolide, three compound. |
| Pharmacological action of original record | Activate the pancreatic function and improve organs constitution, especially the obstruction of electrolytic metabolism of pancreatic gland. Remove the abnormal material in muscle, joint and aponeurosis. Relieve inflammation and promote pus discharge. Modem pharmacological experiments certify that it can inhibit the contraction of skeletal muscle, decrease blood sugar, reduce fever, anti-inflammation, dilate pulmonary vessels and etc. It can markedly increase the antibody produced by ending blood mononuclear cells of healthy human, enhance the immunity and anti-tumor action. |
| Application of pharmacology and goal | Activate the pancreatic function, improve the obstruction of electrolytic metabolism of organs, relieve inflammation and promote pus discharge. |

No: 5

| | | | |
|---|---|---|---|
| Name of Chinese herbs | Shanpeilan | Scientific Name/ Another Name | Eupatorium japonicum thunb, Eupatorium fortunei Trucz, Herba Eupatorii, Foutune eupatorium herb |
| Basis | | | Page of Great dictionary of Chinese medicine, Page 838 Volume 7 of China Ben Cao (Shanghai Science and Technology Publishing House, China) |
| Source, Collect Season, Segment of the plant | | | Taiwan. Cut the above-ground segment, wash clean, half dry in wind, then complete dry under the sun. This plant is different with Eupatorium recorded in Page 1377 of Great dictionary of Chinese medicine and please read Page 838, Volume 7 of China Ben Cao for reference. |
| Processing, Extracting process, Method | | | (1) Take 6 Kg raw materials, wash clean and cut segments. Take 1 Kg raw materials to make dry under the sun, grind them into fine powder. Put another 5 Kg raw materials in pot, add water to infuse them for 3 h, heat and decoct and release the liquid by two times.<br>(2) Heat to evaporate water, mix even with fine powder when it remains 3 Kg raw materials.<br>(3) Dry at 45<br>(4) Crush and grind the materials throughout 120 mesh sieve, then put the fine powder in storage. |
| Active principle | | | Contain volatile oil of 38 kinds such as hexanal, 2-hexenal, borneol, myrtenal, α-famesene and etc as well as germacrene D. The herb contains coumarin, O-coumaric acid and thymohydroquinone. Eupanin, eupachifolin A, B, C, D, E, eupasimplicin A, B and deacetyleupasimplicinA(or B) can be divided from the herb. |
| Pharmacological action of original record | | | Enhance the resistibility against summer fever and diaphoresis; reduce fever, stabilize the function of pancreas, stomach and spleen; promote the electrolytic metabolism of local tissue; promote blood circulation; relieve the toxin in body. Modem pharmacological experiments certify that it has the action against cervical squamous cell carcinoma. |
| Application of pharmacology and goal | | | Stabilize the function of pancreas, stomach and spleen; promote blood and electrolytic metabolism circulation; enhance the goal permeability of organs in the inferior abdominal cavity. |

-continued

No: 6

| | | |
|---|---|---|
| Name of Chinese herbs | Scientific Name/ Another Name | Pericar, pium citri reticulatae, Dried old orange peel, Tangerine Peel, Citrus Paricarpium Reticutata Blanco |
| | Chenpi | |
| Basis | Page 2637 of Great dictionary of Chinese medicine, Page 886 Volume 4 of China Ben Cao (Shanghai Science and Technology Publishing House, China) | |
| Source, Collect Season, Segment of the plant | Fujian. Air-dry Jiangxi's red orange and Fujian's fruit peel, dry them under the sun and keep them in dry and cool place. | |
| Processing, Extracting process, Method | (1) Take dry orange peel 4 Kg, infuse them in light salt solution, cut them into strip, infuse them in the urine of healthy people for 24 h; Take them out and wash clean, rinse off the fetid odor of urine in the clean running water for 24 h; Stir-fry respectively with ginger juice, clean rice, vinegar and salt solution, then dry and grind with 1 Kg into fine powder.<br>(2) Take 3 Kg to put in pot, add water and infuse for 3 h, decoct drug fluid by 2 times.<br>(3) Heat to evaporate water, mix even with fine powder when it remains 3 Kg raw materials.<br>(4) Dry at 45.<br>(5) Crush and grind the materials throughout 120 mesh sieve, then seal off for storage. | |
| Active principle | Primary orange peel contain volatile oil 1.2%–3.19% and its main compounds are limonene, other compounds such as alkene, aldehyde, alcohol and etc. as well as flavones compounds, hesperidin, formamidine hesperetin, β-Sito-sterol, limonin, ferulaic acid and etc. The property of the herb becomes assuasive through urine, vinegar, ginger juice, salt solution, infusing and stir-frying, and enhance the permeability of drug in body. | |
| Pharmacological action of original record | Relax the nervousness of upper digestive tract, increase the appetite, correct the orexia and improve appetite, promote the electrolytic metabolism of alimentary system organs, remove the mucoid material in tissues, smooth the cardia and pyloric nerves, relax the allergy of trachea and bronchus. | |
| Application of pharmacology and goal | Promote the metabolism of tissue fluid, lymphatic fluid and electrolytes, prevent the forming of blood viscosity, regulate the function of pancreas, stomach and bowel, replace the cancerous environment. | |

No: 7

| | | |
|---|---|---|
| Name of Chinese herbs | Scientific Name/ Another Name | Rostellularia, Justicia procumbens(L.)Nees |
| | Juechuang | |
| Basis | Page 2682 of Great dictionary of Chinese medicine, Page 472 Volume 7 of China Ben Cao (Shanghai Science and Technology Publishing House, China) | |
| Source, Collect Season, Segment of the plant | Fujian, Taiwan. Cut the above-ground segment at the booming date of August–September, dry them under the sun. | |
| Processing, Extracting process, Method | (1) Take 6 Kg raw materials, wash clean, cut segment, put in pot, add water and infuse for 3 h, heat and decoct the medicinal liquid by 2 times.<br>(2) Heat to evaporate water, mix even with 1 Kg Fuling powder when it remains 3 Kg concentrated liquid.<br>(3) Dry at 65.<br>(4) Crush and grind the materials throughout 120 mesh sieve, then collect the fine powder for storage. | |
| Active principle | Contain justicidin A, diphyllin, justicidin E, neojusticin A, B, C, D. | |
| Pharmacological action of original record | Regulate and decrease the body temperature on high side, promote the electrolytic metabolism of tissue, remove the obstruction of abnormal material in liver, help the peristalsis of digestive tract, abimtation and anti-inflammation. Modem clinical researches certify that it can effectively cure malaxia, infection urinary system, tubercular anal fistula and etc. | |
| Application of pharmacology and goal | Remove inflammation, clean away toxic materials, promote the electrolytic metabolism, regulate and decrease portal vein pressure. It can be used for treating temperature on high side of straight and large intestines and circulation of lymph system. | |

No: 8

| | | |
|---|---|---|
| Name of Chinese herbs | Scientific Name/ Another Name | Prunella ulgaris L, Prunella Spike, common selfeal fruit-spike, Spica Prunellae, Decumbent Corydalis rhizome, Rhizoma Corydalis Decumbentis, Corydalis decumbens(Thumb) Pers |
| | Xiakucao | |
| Basis | Page 1827 of Great dictionary of Chinese medicine, Page Volume of China Ben Cao (Shanghai Science and Technology Publishing House, China) | |
| Source, Collect Season, Segment of the plant | Jiangsu, Henan, Anhui. Cut the whole plant when flower ear becomes brown on May–June, bundle and dry them under the sun. | |
| Processing, Extracting process, Method | (1) Take 6 Kg raw materials, wash clean, cut segment, put in pot, add water and infuse for 3 h, heat and decoct the medicinal liquid by 2 times.<br>(2) Heat to evaporate water, mix even with 1 Kg Fuling powder when it remains 3 Kg black concentrated liquid.<br>(3) Dry at 65.<br>(4) Crush and grind the materials throughout 120 mesh sieve, then collect the fine powder for storage. | |
| Active principle | The whole herb contains triacanthine. It is oleanolicacid as well as free oleanolicacid, ursolic acid, rutin, hyperoside, caffelcacid, cis-and trans-caffelcacid, Vitamin B1, Vitamin C, Vitamin K, carotene, resin, chrysolepin, volatile oil, alleatloid, water soluble salt (approximately 3.5%, potassium chloride accounts for 68%) and etc. Flower ear contains delphinidin, cyaniding, d-camphor, d-fenchone and ursolic acid. | |
| Pharmacological action of original record | Improve the peripheral blood circulation of eyes, remove the obstruction in liver blood sinus, smooth the circulation of liver, regulate and decrease the portal vein pressure, smooth the lymphatic gland, remove the inflammation of lymph node, remove the symptom of swellen mass. Modem pharmacology has the obvious effect of decreasing blood pressure. Clinical treatment of icteric hepatitis and pulmonary tuberculosis is effective. | |
| Application of pharmacology and goal | Clean away the obstruction of hepatic circulation, improve the metabolism of lymph (specially the hepatic micro-lymph vas), remove the obstruction of abnormal material in the phepatic circulation, phepatic blood-sinus and portal vein wall, regulate and decrease the blood pressure and portal vein pressure based on the pharmacology of Xiakucao's permeability, clean and detoxifeation. | |

No: 9

| | | |
|---|---|---|
| Name of Chinese herbs | Scientific Name/ Another Name | Me sona chinensis benth, Serissa serissoides |
| | Liangfencao | |
| Basis | Page 1915 of Great dictionary of Chinese medicine, Page 87 Volume 7 of China Ben Cao (Shanghai Science and Technology Publishing House, China) | |
| Source, Collect Season, Segment of the plant | Fujian, Taiwan. Reap the above-ground segement in Summer, half dry under the sun, pile to make it zymotic and black, then dry enough under the sun, collect and bundle. | |
| Processing, Extracting process, Method | (1) Take 6 Kg raw materials, wash clean, cut segment. Take 1 Kg from the raw materials to dry under the sun and grind into powder; put another 5 Kg in pot, add water and infuse for 8 h, heat and decoct the medicinal liquid by 2 times.<br>(2) Heat to evaporate water, mix even with powder when it remains 3 Kg concentrated liquid and liquid becomes cool.<br>(3) Dry at 45.<br>(4) Crush and grind the materials throughout 120 mesh sieve, then collect the fine powder for storage. | |

-continued

| | |
|---|---|
| Active principle | The whole herb contains MCPS, mesona chinensis benth polysaccharide (its relative molecular weight is 43000; its hydrolysis products are glucose, glactose, arabinose, xylose, rhamnose, galacturonic acid and an unknown saccharide.) |
| Pharma-cological action of original record | Increase the Yin element in blood, relieve the malaise and disease of the human body caused by the summer fever, remove the radical component of human body, clean away the toxic materials, quench thirst, clean away heat and diminish inflammation. It can treat hypertension, diabetes, the pain in bone resulted from the infection of venereal disease. |
| Application of pharmacology and goal | Reduce fever and detoxify; diminish inflammation; flat and decrease the portal pulse; change the temperature on high side for the cancerous environment; remove the toxins. |

No: 10

| Name of Chinese herbs | Zhizi | Scientific Name/ Another Name | Gardenia jasminoides ellis, Cape jasmine Fruit, Fructus Gardenia |
|---|---|---|---|
| Basis | | | Page 1984 of Great dictionary of Chinese medicine, Page 421 Volume 6 of China Ben Cao (Shanghai Science and Technology Publishing House, China) |
| Source, Collect Season, Segment of the plant | | | Fujian, Taiwan. Reap the herbs in middle and late October when the fruit peel turns yellow-green, get rid of stems and unnecessary things, put them in steam box to make ripe, take out and half dry under the sun, then drying, get rid of fruit peel and keep seed for use. |
| Processing, Extracting process, Method | | | (1) Take 6 Kg raw materials, stir-heat with small fire to dry, crush and grind into powder, put in pot and infuse in the warm water at 70 for 8 h, release the medicinal liquid by 2 times.<br>(2) Evaporate water, mix even with 1 Kg Fuling powder when it remains 3 Kg concentrated liquid.<br>(3) Dry at 65 .<br>(4) Crush and grind the materials throughout 100 mesh sieve, then collect the fine powder for storage. |
| Active principle | | | Contain cyclic olefine ethers compounds of 11 kinds such as gardenoside, geniposide, gardoside and etc., as well as acid compounds of 8 kinds such as chlorogenic acid, crocetin, crocin and etc., ketone compounds of 6 kinds such as rutin, choline and etc. |
| Pharma-cological action of original record | | | Remove the radical element in blood, regulate and decrease the temperature on high side, promote the electrolytic metabolism of body, clear away heat, benefit gallbladder, remove heat toxin. |
| Application of pharmacology and goal | | | Promote the electrolytic metabolism of body, clear away heat, benefit gallbladder, remove heat toxin, regulate and decrease the portal hypertension, smooth the hepatic circulation, remove the inflamed environment of cancers. |

No: 11

| Name of Chinese herbs | Liangiao | Scientific Name/ Another Name | Forsythia suspensa (thunb) vahl, Forsythia Fruit, weeping forsythia capsule, Fructus Forsythiae, capsule of Weeping Frosythia, Frosythia, Weeping Forsythia(fruit) |
|---|---|---|---|
| Basis | | | Page 1111 of Great dictionary of Chinese medicine, Page 155 Volume 6 of China Ben Cao (Shanghai Science and Technology Publishing House, China) |
| Source, Collect Season, Segment of the plant | | | Shanxi, Henan. Reap the herbs in early October when the fruit is ripe and becomes yellow and its shell splits open; dry under the sun, then get rid of seed and impurities. |
| Processing, Extracting process, Method | | | (1) Take 6 Kg raw materials, wash clean, put them into large spun-silk bag and tie the bag, put it in pot with heavy on the bag, infuse in water for 8h, decoct and release the medicinal liquid by 2 times.<br>(2) Heat to evaporate water, mix even with 1 Kg Fuling powder when it remains 3 Kg liquid.<br>(3) Dry at 65 .<br>(4) Crush and grind the materials throughout 100 mesh sieve, then collect the fine powder for storage. |

-continued

| | |
|---|---|
| Active principle | Contain lignin compounds of three kinds such as forsythin, phillyrin and etc., as well as phenylethanes's derivants of three kinds such as rutin, suspensaside and etc., and ethyl cyclohexanols's derivants of six kinds such as rengyolone and etc. It also contains triacid's compounds of six kinds such as betulinic acid, oleanolic acid and etc. |
| Pharma-cological action of original record | Clear away the heat, subdue inflammation, remove the toxin, induce diuresis, open and through the lymph, remove the swollen mass of lymph node. Modem pharmacological experiments certify that Liangiao has a broad-spectrum anti-organism action, subdues inflammation, has the effect against hepatic injury, enhances the strength and tenacity of terminal vessel and prevents bleeding. |
| Application of pharmacology and goal | Open and through lymphatic tissue, improve the change cancerous environment; especially used in clearing away heat, subducing inflammation, clearing away toxin and used for anti-hypertensive of giving the cool. |

No: 12

| Name of Chinese herbs | Chishao | Scientific Name/ Another Name | Paeonia Veitchii Lynch. Red Peony Root, Radix Paeoniae Rubar, Paeonia lactiflora Pall, Unpeeled Root of Herbceous Peony |
|---|---|---|---|
| Basis | | | Page 1093 of Great dictionary of Chinese medicine, Page 521 Volume 3 of China Ben Cao (Shanghai Science and Technology Publishing House, China) |
| Source, Collect Season, Segment of the plant | | | Sichuan. Reap the herbs in August–September; get rid of the above-ground segment and mud, air dry under the sun, then bundle and complete dry under the sun. |
| Processing, Extracting process, Method | | | (1) Take 5 Kg Chuan Chishao, wash clean, cut it into small pieces, put it in pot and infuse in water for 3 h, heat and decoct and release the medicinal liquid by 2 times.<br>(2) Heat to evaporate water, mix even with 1 Kg Fuling powder when it remains 3 Kg liquid.<br>(3) Dry at 65 .<br>(4) Crush and grind the materials throughout 100 mesh sieve, then collect the fine powder for storage. |
| Active principle | | | Chuan Chishao root contains Daeoniflorin, and products produced in Sichuan also contains trace benzoyl paconiflorin. |
| Pharma-cological action of original record | | | Promote the blood circulation, remove the thrombus, regulate and decrease the blood temperature, clear away heat. Modem pharmacological experiments certify that it can subdue the thrombus forming, against the platelet agglutination, decrease the blood lipid and restrain the atheroselerosis against the tumor, nourish the liver, improve the blood circulation action. |
| Application of pharmacology and goal | | | Promote the blood circulation, open and through the lymphatic tissue of the organs in lower abdomen cavity, improve the cancerous goal environment with other medicine. |

No: 13

| Name of Chinese herbs | Dahuang | Scientific Name/ Another Name | Pheum pulmatum L, Rhubarb, Radix et Rhizoma Rhei, Rheum palmarum, Rheum tanguticum Maxim et Balf, Rheum of ficinale |
|---|---|---|---|
| Basis | | | Page 102 of Great dictionary of Chinese medicine, Page 708 Volume 2 of China Ben Cao (Shanghai Science and Technology Publishing House, China) |
| Source, Collect Season, Segment of the plant | | | Sichuan. Reap the root and rhizome; get rid of the scarf-skin and arrange the herb, 1/4 cool dry indoor, then drying with fire. |

-continued

| | |
|---|---|
| Processing, Extracting process, Method | (1) Take 4 Kg Dahuang, wash clean, cut it into small pieces, 1 Kg for drying and grinding into powder, put another 3 Kg in pot, infuse in water for 8 h, heat and decoct out medicinal liquid by 2 times.<br>(2) Heat to evaporate water, mix even with powder when it remains 3 Kg concentrated liquid.<br>(3) Dry at 65 .<br>(4) Crush and grind the materials throughout 120 mesh sieve, then collect the fine powder for storage. |
| Active principle | Active principle accounts for 2.034%–2.984% of the total weight, in which emodin content accounts for 0.037%–1.155% and conjugated emodin content accounts for 1.829%–1.997%. It also contains dibenzo ketones of 4 kinds such as palmidin A, B, C and etc., as well as stilbene compounds, resin, catechin, epicatechin gallate, glucogallin and etc. |
| Pharmacological action of original record | The original record accords with the modem pharmacological research. In the alimentary system, it can nourish the liver, benefit the gallbladder, against the gastic and duodenal ulcer, prevent the absorption of water in the colon, quicken the removing of subslance, induce diarrhea action, have the anti-bacterial, anti-viral, anti-fungal action |
| Application of parmacology and goal | Nourish the liver, benefit the gallbladder, anti-viral, remove the toxic material in body. |

No: 14

| | | |
|---|---|---|
| Name of Chinese herbs | Scientific Name/ Another Name<br>Zhechong | Eupolyphoqa sinensis walker, Blister Beetle, Large Blister Beetle, Mylabris, Mylabris phalerate Pallas |
| Basis | | Page 2684 of Great dictionary of Chinese medicine, Page 151 Volume 9 of China Ben Cao (Shanghai Science and Technology Publishing House, China) |
| Source, Collect Season, Segment of the plant | | Henan. After catching it, make it dead with boiling water, dry under the sun. |
| Processing, Extracting process, Method | | (1) Take 4 Kg Zhechong, infuse and clean in rice wine of 18 degree, stir-fry to make it dry and light yellow with small fire, then take the 1 Kg to grind into fine powder, put another 3 Kg in pot and infuse in water for 3 h, heat and decoct out the medicinal liquid by 2 times.<br>(2) Heat to evaporate water, mix even with powder when it remains 2 KL concentrated liquid.<br>(3) Dry at 60 .<br>(4) Crush and grind the materials throughout 120 mesh sieve, then collect the fine powder for storage. |
| Active principle | | Contain fatty acids of many kinds as well as amino acids of 17 kinds such as glutamic acid and etc., blood plasminogen promotor, alcohols compounds such as alkaloid, cholesterol and etc. It also contains inorganic elements of 28 kinds such as K, Mg, Ca, Zn, P and etc., uracil and allantoin. |
| Pharmacological action of original record | | Have anit-coagulant action, remove the thrombus in the blood vessel, improve the obstruction of the tendinous sheath and costal pleura. Modem Pharmacology: directly dilatate blood vessel, anti-coagulant action, relieve the forming of atherosclerosis. |
| Application of pharmacology and goal | | Open and through the circulation of screw artery, micro-blood vessel, relieve the thrombus, remove the dead cancerous cells or toxic materials combined with other drug therapy. |

No: 15

| | | |
|---|---|---|
| Name of Chinese herbs | Bai Huashe-shecao | Scientific Name/ Another Name | Oldenlandia jiffusa (wild) roxb, Olderlandia, Spreading Hedoyotis herb, herba Hedyotis Diffusea, Hedyotis diffusa Willd, Herb of Spreading Hedyotis |
| Basis | | Page 754 of Great dictionary of Chinese medicine, Page 433 Volume 6 of China Ben Cao (Shanghai Science and Technology Publishing House, China) |

-continued

| | |
|---|---|
| Source, Collect Season, Segment of the plant | Anhui, Guangxi and provinces in China's southeast coast. Reap the herb in Summer and Autumn, wash clean, dry under the sun, keep in cool and dry place. |
| Processing, Extracting process, Method | (1) Take 6 Kg Bai huashe-shecao, put in pot and infuse in water for 3 h, heat and decoct out the medicinal liquid by 2 times.<br>(2) Heat to evaporate water, mix even with 1 Kg Fuling powder when it remains 3 KL concentrated and black liquid.<br>(3) Dry at 65 .<br>(4) Crush and grind the materials throughout 120 mesh sieve, then collect the fine powder for storage. |
| Active principle | Contain asperuloside, asperulosidic acid, deacetylasperulosidic acid, pederin and ursolic acid, β-sitosterol, hentriacontane, stigmasterol, oleanolic acid, p-coumaric acid. |
| Pharmacological action of original record | Clear away the temperature on high side resulted from the radical elements, relieve toxin, promote the circulation of electrolytic metabolism of local tissues and specially the organs in lower abdominal cavity. Modem pharmacological experiments certify that it can enhance the white corpuscles engulf function, increase the immunize function, anti-bacterial and anti-tumor actions, do good to gastric carcinoma and carcinoma of the rectum. |
| Application of pharmacology and goal | Clear away the radical elements and toxic materials, promote the circulation of electrolytic metabolism and lymph circulation. According to the application experience, it can promote the function of lymphocytes aggregated in small intestine (Payer's patches) and iliac lymph node. |

No: 16

| | | |
|---|---|---|
| Name of Chinese herbs | Gangbanggui | Scientific Name/ Another Name | Polygonum per foliatum L. |
| Basis | | Page 869 of Great dictionary of Chinese medicine, Page 685 Volume 2 of China Ben Cao (Shanghai Science and Technology Publishing House, China) |
| Source, Collect Season, Segment of the plant | | Fujian, Taiwan. Reap the herb and rhizome, wash clean, cut in segments, cool dry. |
| Processing, Extracting process, Method | | (1) Take 6 Kg, wash clean, put in pot and infuse in water for 8 h, heat and decoct out the medicinal liquid by 2 times.<br>(2) Heat to evaporate water, mix even with 1 Kg Fuling powder when it remains 3 KL liquid.<br>(3) Dry at 65 .<br>(4) Crush and grind the materials throughout 120 mesh sieve, then collect the fine powder for storage. |
| Active principle | | Contain kaempferol, caffeic acid methyl ester, quercetin, caffeic acid, protocate chuic acid, quercetin-3-β-D-glucuronide methylester, P-coumaric acid, ferulic acid, Vanillicacid, ursolic acid, betulic acid, betulin, Phytosteryl-β-D-glucoside, 3,3',4,4'-tetramethylellagic acid, 3,3'-dimethylellgic acid, dimethyl mesotartrate, long-chain aliphatic ester, indican and tannin. The root and rhizome contains a few e-modin and chrysophand. |
| Pharmacological action of original record | | Promote the electrolytic metabolism of body, induce diuresis, relieve swollen, reduce fever, clear away thrombus and toxin in tissues. It is used in treating gonorrhea, venereal infective disease and ascites diseases. Modem pharmacological experiments certify that it has the anti-bacterial, anti-viral and anti-tumor actions. |
| Application of pharmacology and goal | | Combined with other drugs, enhance anti-bacterial, anti-viral, and anti-tumor effectiveness, promote the pharmacology of electrolytic metabolism, quicken and remove out the toxic materials from body. |

No: 17

| | | |
|---|---|---|
| Name of Chinese herbs | Shandougen | Scientific Name/ Another Name | Sophora tonkinensis Gagnep, Subprostrate Sophora Root, Tonkin Sophora Root, Radix Sophorae Tonkinenensis, Root of Subprostrate, Root of Tonkin Sophora |

| | | |
|---|---|---|
| Basis | Page 181 of Great dictionary of Chinese medicine, Page 652 Volume 4 of China Ben Cao (Shanghai Science and Technology Publishing House, China) | |
| Source, Collect Season, Segment of the plant | Guangxi. Reap the root in Autumn, get rid of impurities, wash clean and dry under the sun. | |
| Processing, Extracting process, Method | (1) Take 5 Kg, wash clean, infuse and cut in segments, then take 1 Kg for drying and grinding into powder, put another 4 Kg in pot and infuse in water for 8 H, heat and decoct out the medicinal liquid by 2 times.<br>(2) Heat to evaporate water, mix even with original powder when it remains 3 KL liquid.<br>(3) Dry at 65 .<br>(4) Crush and grind the materials throughout 120 mesh sieve, then collect the fine powder for storage. | |
| Active principle | Contain matrine, oxymatrine, Anagyrine, methylcytisine and etc., flavones compositions of all kinds, sophoranone, sophoradin, sophoranochromene, sophoradochromene, genistein, pterocarpine, maackian, trifolirhizin, chitosterol, Sitosterol, Lu-peol, caffeic acids and the unknown cyan fluorescence material. | |
| Pharmacological action of original record | Clear away the radical elements of body (bring down the fever), neutralize toxic elements (remove the toxic material), alleviate the record laryngeal inflammation and edema, ease pain, kill the intestinal parasites. Modem pharmacology: contain alkaloids of all kinds and have the anti-tumor action. | |
| Application of pharmacology and goal | Clear away the radical elements, neutralize the toxic elements, decrease the load of defense system. | |

No: 18

| | | |
|---|---|---|
| Name of Chinese herbs | Mujinpi | Scientific Name/ Another Name | Hibiscus syriacus L, Shrubalthea Bark, Hibiscus, Shrubalthea |
| Basis | Page 366 of Great dictionary of Chinese medicine, Page 357 Volume 5 of China Ben Cao (Shanghai Science and Technology Publishing House, China) | |
| Source, Collect Season, Segment of the plant | Taiwan. Reap the above-ground segment in April–May, get rid of flowers, leaves, young branches, only remain the stem of over the size of little finger, destroy the hard bones with heavy equipment, take the cortex and cut in segments, dry under the sun. | |
| Processing, Extracting process, Method | (1) Take 5 Kg, wash clean, put in pot and infuse in water for 8 h, heat and decoct out the medicinal liquid by 2 times.<br>(2) Heat to evaporate water, mix even with 1 Kg Fuling powder when it remains 3 KL liquid.<br>(3) Dry at 45 .<br>(4) Crush and grind the materials throughout 120 mesh sieve, then collect the fine powder for storage. | |
| Active principle | Contain suberic acid, 1-octacosand, β-sitosterol, 1,22 docosanediol, betulin, erythrotriol, nonanedioic acid, as well as fatty acids which include myristic acid, palmitic acid and laurie acid, and canthin-6-one. | |
| Pharmacological action of original record | Regulate and decrease the temperature on high side in lung and large intestine, dilute the mucus in tissue, anti-bacterial, kill parasites, have effect upon the treatment of abscess of lung (lung tumor). Modern pharmacology tells us that the erythrotriol of monomer compounds of 7 kinds divided from Mujinpi can inhibit the action of the tumor cells' reproduction. | |
| Application of pharmacology and goal | Regulate and decrease the temperature on high side in lung and large intestine, dilute the mucus in lymphatic tissue in order to improve the defense function. According to the experience of curing lung tumor in ancient books and modem pharmacology, that combined with other drugs, directly make effect on cancerous cells in lung, intestine and etc., can improve and change the cancerous environment. | |

No: 19

| | | |
|---|---|---|
| Name of Chinese herbs | Tiannanxing | Scientific Name/ Another Name | Arisaema heterophyllum B1, Rhizome of Arisaema |
| Basis | Page 329 of Great dictionary of Chinese medicine, Page 504 Volume 8 of China Ben Cao (Shanghai Science and Technology Publishing House, China) | |
| Source, Collect Season, Segment of the plant | Jiangxi. Dig out tuber in October, get rid of mud and stem, leaves and fibrous root, put them in the special bag (cask type pharmacy appliance) and ram and rub the herb in order to get rid of coat, then take out and wash clean, smooth its surface with bamboo knife, finally fumigate it with brimstone to make it white and then dry under the sun. | |
| Processing, Extracting process, Method | (1) Take approximate 3 Kg herb grains, infuse and clean in water, change water for 2–3 times a day. When there's white foam, change water and add 120 mg alumen to the water, then change water after infusing in such water for one day. Take out until it has the small insensitive taste.<br>(2) Take the infused Tiannanxing and add 1 Kg fresh ginger, then put in pot and cook for 4 H, take out and cool dry of 80%, cut into pieces and dry under the sun.<br>(3) Take 1 Kg to be grinded into powder, put another 2 Kg in pot and infuse in water for 3 H, heat and decoct out the medicinal liquid by 2 times.<br>(4) Heat to evaporate water, mix even with original powder when it remains 2.5 Kg liquid.<br>(5) Dry at 65 .<br>(6) Crush and grind the materials throughout 120 mesh sieve, then collect the fine powder for storage. | |
| Active principle | Contain alkaloids of all kinds such as L-prolyl-L-valine anhydride, uracil, thymine, nicotinamide and etc., cyclic diolefine compounds and pedatisectine A, B, C, D, E, as well as daucosterol, β-stitosterol, palmitic acid and amino acids of 30 kinds such as proline and inorganic trace elements of over 20 kinds. | |
| Pharmacological action of original record | Eliminate the initiative pathogenic factors of blood vessel and micrangium pressure, allay excitement, relieve muscular spasm, clear sputum, dilute the mucus in tissue, open and through lymphatic tissue. Modem pharmacological experiments certify that it can have the directly killing or inhibitive action for cancers of lung, liver, stomach, uterus and etc. | |
| Application of pharmacology and goal | Regulate the normal pressure of microangium, dilute the viscosity of tissue fluid and pass through lymphatic tissue. Combined with other drugs, it can improve the changed cancerous environment. | |

No: 20

| | | |
|---|---|---|
| Name of Chinese herbs | Banbianlian | Scientific Name/ Another Name | Lobelia chinensis lour, Chinese Lobelia Lour, Chinese Lobelia herb, Herb Lobeliae chinensis, Herb of Chinese lobelia |
| Basis | Page 754 of Great dictionary of Chinese medicine, Page 613 Volume 7 of China Ben Cao (Shanghai Science and Technology Publishing House, China) | |
| Source, Collect Season, Segment of the plant | Anhui, Fujian, Taiwan. Reap the complete herb, wash clean and cool dry under the sun. | |
| Processing, Extracting process, Method | (1) Take 4 Kg Banbianlian, put in pot and infuse in water for 3 H, heat and decoct out the medicinal liquid by 2 times.<br>(2) Heat to evaporate water, mix even with 1 Kg Fuling powder when it remains 3 Kg concentrated liquid.<br>(3) Dry at 65 .<br>(4) Crush and grind the materials throughout 120 mesh sieve, then collect the fine powder for storage. | |

-continued

| | |
|---|---|
| Active principle | Contain alkaloids which mainly are L-lobeline, lobelanine, lobelanidlne, isobelanine (or demethylobelanine), flavonol, saponin, amino acids, amylose, inulin, p-hydroxyacid and succinicacid. The rhizome contains lobelinin. |
| Pharmacological action of original record | Regulate and decrease the temperature on high side in the tissue, start the defence organs, promote the function of relieving toxin, enhance the electrolytic metabolism, eliminate ascites and swelling of foot and leg, smooth the lymph metabolism, neutralize the toxin material. Modern pharmacology: diuresis, against snake venom and etc. it can treat ascites of hepatocirrhosis and carcinoma of many kinds. |
| Application of pharmacology and goal | Smooth the lymph circulation in the inside of organs; start defense organs and promote the function of detoxification. In 1976, the originator published Banbianlian's Research and Application which explains the efficiency in therapy, but can't be accepted for some certain reasons; The article Toxicity described it was collected in Taiwan noxious Plants. |

No: 21

| | | | |
|---|---|---|---|
| Name of Chinese herbs | Bailian | Scientific Name/ Another Name | Ampelopsis joponica (thunb) makino, Ampelopsis Japanese Root, Ampelopsis, Radix Ampelopsis, Japanese Ampelopsis, Root of Japanese Ampelopsis |
| Basis | | | Page 691 of Great dictionary of Chinese medicine, Page 276 Volume 5 of China Ben Cao (Shanghai Science and Technology Publishing House, China) |
| Source, Collect Season, Segment of the plant | | | Anhui, Jiangxi. Reap and dig out the herb in Spring and Autumn, get rid of stem and fibrous root, wash clean, cut into two pieces, dry under the sun. |
| Processing, Extracting process, Method | | | (1) Take 6 Kg, wash clean, take 1 Kg for grinding into fine powder. Take another 5 Kg for grinding into-powder, put in pot and infuse in water, heat under the temperature limit of 70 for 3 H and release the medicinal liquid by 3 times. (2) Heat to evaporate water, mix even with 1 Kg original fine powder when it remains 3 KL concentrated liquid. (3) Dry at 65. (4) Crush and grind the materials throughout 120 mesh sieve, then collect the fine powder for storage. |
| Active principle | | | Contain viscous material, starch, tartaric acid, β-sitosterol, fumaric acid, daucosterol. |
| Pharmacological action of original record | | | Regulate and decrease the abnormal temperature on high side, promote the toxic action of the lymph node and other defense systems, relax the tightening state of ligament of organs and connective tissues, quicken the healing of tissue ulcer. Modem pharmacological experiments certify that it has the anti-bacterial action. The Bailian described by Li Guangxun in 1992 and experiments certify that it has inhibitive action of cervix cancerous cells culture of human JTC-26 and therefore it has the anticancer effect. |
| Application of pharmacology and goal | | | Deep into the lymph and defense tissue to relax and remove the toxic materials. Combined with other drugs, change the cancerous environment. |

No: 22

| | | | |
|---|---|---|---|
| Name of Chinese herbs | Loulu | Scientific Name/ Another Name | Echinops latifolius tausch, Globethistle(root), Uniflower swisscentaury root, Radix Rhapontici, Rhaponticum uniflorum(L)DC., Root of Broadleaf Globethistle, Root of Uniflower Swisscentaury |
| Basis | | | Page 2576 of Great dictionary of Chinese medicine, Page 976 Volume 7 of China Ben Cao (Shanghai Science and Technology Publishing House, China) |
| Source, Collect Season, Segment of the plant | | | Shandong, Henan, Taiwan (Ali Mountain). Reap after Autumn, get rid of mud, stem and ete, keep the underground rhizome and dry under the sun for use. |

-continued

| | |
|---|---|
| Processing, Extracting process, Method | (1) Take 6 Kg, infuse and dry, cut into pieces, take 1 Kg for grinding into powder. Put another 5 Kg in pot and infuse in water for 3 H, heat and decoct and release the medicinal liquid by 2 times. (2) Heat to evaporate water, mix even with 1 Kg original powder when it remains 3 KL liquid. (3) Dry at 45. (4) Crush and grind the materials throughout 100 mesh sieve, then collect the fine powder for storage. |
| Active principle | Contain volatile oils of 24 kinds such as limonene, menthone, and etc., as well as ziyugluooside, taraxerol acetate, ursonicacid, triacontanoic acid, β-sitosterol and daucosterol. |
| Pharmacological action of original record | Promote the blood circulation and lactescence of lying-in woman, decrease the temperature on high side of human. body, enhance the detoxifcation function of defense system. Modem pharmacological experiments certify that it has the anti-atherogenic, anti-oxidative, nourishing liver and immunization improving actions and etc. |
| Application of pharmacology and goal | Many drugs, which can promote the lactescence of lying-in woman, are found to have the action to promote lymphatic circulation. This herb is such a drug. External disease and pyogenic infections, mastitis, scrofula, hemorrhoid and etc., all concern with lymph nodes. The main goal is to open and through the Peyer's patches, intestine and bone lymph nodes, lymphonodulus in order to open and through lymph in kidney and lower abdominal cavity. |

No: 23

| | | | |
|---|---|---|---|
| Name of Chinese herbs | Shiwei | Scientific Name/ Another Name | Pyrrosia sheareri (Bak) ching, Pyrrosia Leaf, Pyrrosia sheareri (Bak) ching, Japanese felt fern leaf, Folium Pyrrosiae, Pyrrosia lingua (Thub.) Farwell |
| Basis | | | Page 579 of Great dictionary of Chinese medicine, Page 253 Volume 2 of China Ben Cao (Shanghai Science and Technology Publishing House, China) |
| Source, Collect Season, Segment of the plant | | | Lushan Shiwei, Taiwan and Fujian. Reap in whole year, wash clean, half dry under the sun and then cool dry. |
| Processing, Extracting process, Method | | | (1) Take 8 Kg Shiwei, put in pot and infuse in water for 8 H, heat and decoct and release the medicinal liquid by 2 times. (2) Heat to evaporate water, mix even with 1 Kg Fuling powder when it remains 3 KL liquid. (3) Dry at 65. (4) Crush and grind the materials throughout 120 mesh sieve, then collect the fine powder for storage. |
| Active principle | | | Contain diploptene, mangiferin, vanillic acid, protocatechuic acid, Furnaric acid, caffeic acid, β-sitosterol, sucrose, isomangiferin and chlorogenic acid. |
| Pharmacological action of original record | | | Relax the tension of prostata, induce diuresis, relieve and remove the inflammation symtom of bladder, urethra and prostata, treat the bleeding of bladder and urethra, inhibit the action of bacterium and virus of many kinds in the lower abdomen cavity. The mangiferin has the stronger resistance against the Herpes Simple Virus, prevents the replication of virus at cells. It can raise leucocyte amount for the leukopenia status resulted from chemotherapy and radiotherapy. Enhance the effectiveness of phagocytes in body. |
| Application of pharmacology and goal | | | Improve the inflammation of lower celiac organs and decrease the symptom. Combined with other drugs, enhance the defense function. |

No: 24

| | | | |
|---|---|---|---|
| Name of Chinese herbs | Ruxiang | Scientific Name/ Another Name | Boswellig carterii Birdw. Frankincense, Olibanum, Olibanum Gum |
| Basis | | | Page 1379 of Great dictionary of Chinese medicine, Page 17 Volume 5 of China Ben Cao (Shanghai Science and Technology Publishing House, China) |

| | | |
|---|---|---|
| Source, Collect Season, Segment of the plant | Import herb mainly produced in Greece and Turkey and etc., it's the resin from Ruxiang by cutting its cortices. | |
| Processing, Extracting process, Method | (1) Ruxiang is prepared by Juncus, take 4 Kg, put in pot and infuse in water for 3 H, heat and decoct and release the medicinal liquid by 2 times. (2) Heat to evaporate water, mix even with 1 Kg Fuling powder when it remains 3 KL chyle-colouring concentrated liquid. (3) Dry at 50. (4) Crush and grind the materials throughout 100 mesh sieve, then collect the fine powder for storage. | |
| Active principle | Ruxiang wood contains resin 60%–70%. Its main compositions are free α,β-boswellicacid 33% and olibanoresene 33%, contains resin 27%–35%. The resin is 20% arabicacid calcium and magnesium, 3%–8% volatile oil which is light yellow and fragrant, composed of alkenes, aldehydes, ketones of many kinds. | |
| Pharmacological action of original record | Promote the circulation of blood and lymph fluid, remove the abnormal aggregation of lymph and thrombus in tissue, ease pain and diminish swelling. | |
| Application of pharmacology and goal | Promote the normal circulation of blood and lymph fluid, improve the function of defense organs. Combined with other drugs, it can remove the thrombus, cancerous cells and other foreign matters. | |

No: 25

| | | |
|---|---|---|
| Name of Chinese herbs | Scientific Name/ Moyao Another Name | Commiphora Myrrha Engi, Myrrha, Myrrh, Common Myrrh Tree |
| Basis | Page 1167 of Great dictionary of Chinese medicine, Page 26 Volume 5 of China Ben Cao (Shanghai Science and Technology Publishing House, China) | |
| Source, Collect Season, Segment of the plant | Somalia. Burseraceac, oil resin oozing from the bark of trees, imported Chinese herbs since ancient times | |
| Processing, Extracting process, Method | (1) The Mayao is prepared by Juncus effuses L. Var. Put in pot with Mayao 4 kg, and add water and infuse for 3 hours, heat and decoct out medicinal fluid by 2 times. (2) Heat to evaporate water, when it remains 3 KLd concentrated liquid, add 1 kg Fuling power, stir and mix up. (3) Dry at 50 (4) After cooling, crush and grind throughout 100 mesh sieve, then collect the fine powder for sealing up and storage. | |
| Active principle | Content: Resin 25–35%, 2.5–9% volatile oil, 57%–65% balata. Hydrolyzeing products are arabinose, galactose, and xylose. Volatile oil is easy resinifying at air, and it contains phenol, aldehyde, as well as multi-furanosides compounds. | |
| Pharmacological action of original record | Promote the blood circulation, remove the obstruction of foreign mater in circulation to dredge the obstruction and achieve effect of alleviation. Clear away the abnormal swelling of connective tissue. According to the modem pathology research, it can regulate and decrease blood lipid and cholesterol, prevent the forming action of atherosclerosis, inhibit the forming of the cholesterol of hepatic homogenate. | |
| Application of pharmacology and goal | Promote the normal circulation of blood, combined with other drugs, it can remove toxic matters, such as bacterium, cancerous factors etc. | |

No: 26

| | | |
|---|---|---|
| Name of Chinese herbs | Zao xiu | Scientific Name/ Another Name P. chinesis Franch |
| Basis | Page 1748 of Great dictionary of Chinese medicine, Page 130 Volume 8 of China Ben Cao (Shanghai Science and Technology Publishing House, China) | |
| Source, Collect Season, | Fujian, Taiwan, Pick up in Sep.–Oct, when the leaves are blasted, dig out roots, sunlight dry or drying, remove | |
| Segment of the plant | rough skin and fibrous root. | |
| Processing, Extracting process, Method | (1) Zaoxiu 4 kg, wash clean, cut slice, take 1 kg and put over a slow fire to dry; put another 3 kg in pot and add water, infuse for 3 hours, heat and decoct out medicinal fluid by 2 times. (2) Heat to evaporate water, when it remains 3 KL concentrated liquid, add drug power, stir and mix up. (3) Dry at 65. (4) Crush and grind throughout 120 mesh sieve, collect fine power for storage | |
| Active principle | The root and stem contain {diosgenin-3-o-α-L-arabino-furanosyl (14)-[α-L-rhamnopyranosyl (12)]-}-β-D-glucopyranoside}, as well as other compositions: saponins, glycogly, glucoside, etc. | |
| Pharmacological action of original record | Allay excitement, open and through the lymph organs and defense tissue, remove the foreign matter in it, clear away the inflammation symptoms in the organs, tissues and liver. | |
| Application of pharmacology and goal | Open and through the lymph organ and defense tissue, remove the foreign matter in it. | |

No: 27

| | | |
|---|---|---|
| Name of Chinese herbs | Baijiang | Scientific Name/ Another Name | Patrinia Villosa (thunb.) juss. Whiteflower Patrinia Herb, Herba Patriniae, Patrinia |
| Basis | Page 1340 of Great dictionary of Chinese medicine, Page 570 Volume 7 of China Ben Cao (Shanghai Science and Technology Publishing House, China) | |
| Source, Collect Season Segment of the plant | Sichuan, Fujian. Pick in Summer, pull out the whole herb, clean and dry under the sun. | |
| Processing, Extracting process, Method | (1) Take 8 kg, wash clean, cut segment, put in pot and add water, infuse for 8 hours, heat and decoct out medicinal fluid by 2 times. (2) Heat to evaporate water, when it remains 3 KL concentrated liquid, add Fuling power 1 kg, stir and mix up. (3) Dry at 45 (4) Crush and grind throughout 120 mesh sieve, collect powder for storage. | |
| Active principle | The white flower consists of villososide, loganin, morroniside, vilosol, villosolside, oleanolic acid, palmiticacid as well as inositol. | |
| Pharmacological action of original record | Regulate and decrease temperature on high side, promote the anti-toxic function of defense system, clear away the thrombus, pus fluid; as well as tranquilization, anti-bacterial and antiviral action in modem pathology. The trial report in 1992 issued by Gao Shujuan shows that if pure (100%) patrima is added into the 10 mg endotoxin, can decrease toxic activity, with detoxic rate is 8.7%. | |
| Application of pharmacology and goal | The pharmacological action of patrinia at lower abdomen organs is most remarkable, used to cool and refreshing, allay fever, drain pus and remove the poisonous substance, promote the normalization of local circulation. | |

No: 28

| | | | |
|---|---|---|---|
| Name of Chinese herbs | Baizhi | Scientific Name/ Another Name | Angelica dehurica, Angelica, Angelica dehurica (Fisch ex Holfm.), Radix Angelica Dahuricae, Dahurican angelica root, Dahurican Angelica, Dahurican Angelica Root, Root of Taiwan Dahurican Angelica |
| Basis | Page 675 of Great dictionary of Chinese medicine, Page 883 Volume 5 of China Ben Cao (Shanghai Science and Technology Publishing House, China) | | |
| Source, Collect Season, Segment of the plant | Sichuan, Zhejiang. In late Aug.–Otc, pick when the leaves blasted, get rid of mud and drying. | | |

| | |
|---|---|
| Processing, Extracting process, Method | (1) Take 6 Kg, wash clean, cut segment, 1 Kg is griended to fine power, put another 5 Kg in pot and add water, infuse, heat with 70 as the most highest temperature for 8 H, decoct out medicinal fluid by 3 times.<br>(2) Heat to evaporate water, when it remains 3 KL yellow concentrated liquid, add drug power 1 Kg, stir and mix up.<br>(3) Dry at 45 .<br>(4) Crush and grind throughout 120 mesh sieve, collect fine power for storage. |
| Active principle | Consists of imperatorial ostruthiums of four kinds such as imperatorin, peucedanins of three kinds such as oxypeucedanin, many coumarins' composition such as byakangelicin, brakangclicol, neobyalkangclicol, phellopterin, xanthotoxol, bergapten, cnidilin, pabulenol and etc., sitosterol, palmitic acid as well as 11 elements including Na., Mg, Ca, Fe, P, etc. |
| Pharmacological action of original record | Antimicrobial action, treat the cold and wind-cold syndrome, relieve inflammations, reduce fever, remove the pathogenic factors of producing micro-blood vessel's abnormal pressure (eliminate wind), promote the electrolytic metabolism of tissue (dispel dampness), remove the inflammation and swelling of mucous membrane in nasal and pharynx cavity, ease pain. |
| Application of pharmacology and goal | Guide the other drugs into head and thoracic cavity. Promote the effect of anti-cancerous and treating cancerous, remove the pathogenic factors of producing micro-blood-vessel's abnormal pressure, improve the electrolytic metabolism in tissue, defense the invading and attack of external circulation. |

No: 29

| | | | |
|---|---|---|---|
| Name of Chinese herbs | Shegan | Scientific Name/ Another Name | Belameanda chinensis (L.) DC, Belamcanda Rhizome, Blackberry lily rhizome, Rhizoma, Belamcandae, Blackberry lily (rhizome), Rhizome of Blackberry lily |

| | |
|---|---|
| Basis | Page 1883 of Great dictionary of Chinese medicine, Page 256 Volume 8 of China Ben Cao (Shanghai Science and Technology Publishing House, China) |
| Source, Collect Season, Segment of the plant | Fujian, Taiwan. Dig out root in Spring or Autumn, clean and half-dry and remove fibrous root, then dry it thoroughly |
| Processing, Extracting process, Method | (1) Take 5 Kg, wash clean, put into the thick liquid (rice-sup refers to water-infused rice by 24 hours), infuse for 24 hours, take out and rinse clean with water, then cut segment, put in pot, add water and infuse, heat and decoct out medicinal fluid by 2 times.<br>(2) Heat to evaporate water, when it remains 3 KL time, add 1 Kg Fuling power, stir and mix up.<br>(3) Dry at 65 .<br>(4) Crush and grind throughout 120 mesh sieve, collect fine power for storage. |
| Active principle | Consist of belamcandin, lridin, tectoridin, tectorigenin and so on. |
| Pharmacological action of original record | Against the inflammation, reduce fever, remove the sputum, clear away throat pain, open and through out lymph, remove and dissolve scrofula. Recorded in ancient books, it can treat the lump of liver and pancreas (the mother of malaria, mass located in the upper abdomen) effectively, while in modem medicine, it can relieve inflammation, reduce fever, clear sputum, resist the microbial (Bacillus anthracis, Bacterium diphtheria, typhoid bacillus, human bacillus, tubercle), and influenza virus, etc. |
| Application of pharmacology and goal | Open and through out lymph, anti-inflanimation, reduce fever, remove sputum, against and kill the part microorganism of body, improve the abominable environment, increase the defense function and process. |

No: 30

| | | | |
|---|---|---|---|
| Name of Chinese herbs | Pugongying | Scientific Name/ Another Name | Taraxuacum mongoliem Hand Mazz, Dandelion Herb, Dandelion, Herb Taraxaci, Taraxacum |

| | |
|---|---|
| Basis | Page 2459 of Great dictionary of Chinese medicine, Page 986 Volume 7 of China Ben Cao (Shanghai Science and Technology Publishing House, China) |
| Source, Collect Season, Segment of the plant | Fujian, Taiwan. Dig out with root before blooming and starting blooming in April–May, clean and dry under the sun. |
| Processing, Extracting process, Method | (1) Take 6 Kg, wash clean, put in pot, add water and infuse for 3 hours, heat and decoct out medicinal fluid by 2 times<br>(2) Heat to evaporate water, when it remains 3 KL time, add Fuling power 1 kg, stir and mix up.<br>(3) Dry at 65 .<br>(4) Crush and grind throughout 120 mesh sieve, collect fine power for storage. |
| Active principle | Consist of taraxasterol, choline, inulin, pectin, ect. |
| Pharmacological action of original record | Promote the permeability in lymph tissue, clear away the toxic material of body, regulate the temperature on high side, against the inflammation, remove general anasarca. Modem pharmacology explains that it can resist the pathogenic micro-organism, resist gastric ulcer, benefit gallbladder, nourish the liver, start the effectiveness of macro-phagocyte and anti-tumer. |
| Application of pharmacology and goal | Effective herb for treating swelling of lymph node, promote the permeability in the lymph tissue. Combined with other drugs, it can remover the lymph endotoxin, temperature on high side, inflammation and swelling. |

No: 31

| | | | |
|---|---|---|---|
| Name of Chinese herbs | Luoyancao | Scientific Name/ Another Name | Lemmaphyllum microphyllum presl, Adiantum Flabellulatum |

| | |
|---|---|
| Basis | Page 1322 of Great dictionary of Chinese medicine, Page 228 Volume 2 of China Ben Cao (Shanghai Science and Technology Publishing House, China) |
| Source, Collect Season, Segment of the plant | Taiwan, named as Baoshulian (Dryrnoglossum piloselloides) in Great dictionary of Chinese medicine. Reap in whole year, wash clean and dry under the sun. |
| Processing, Extracting process, Method | (1) Take 6 Kg, wash clean, put in pot and infuse in water for 8 H, heat and decoct and release the medicinal liquid by 2 times.<br>(2) Heat to evaporate water, mix even with 1 Kg Fuling powder when it remains 3 KL liquid.<br>(3) Dry at 65 .<br>(4) Crush and grind the materials throughout 120 mesh sieve, then collect the fine powder for storage. |
| Active principle | Contain compound of 7 kinds such asα-onoceradiene, steroids of three kinds such as pterosterone. |
| Pharmacological action of original record | Clear away the radical composition in body, regulate and decrease the temperature on high side, promote the function of electrolytic metabolism, induce diuresis, assist the function of defence, anti-toxin, killing intestinal parasites. The ancient books record that it can clear away the swollen lump in the lower abdominal cavity, scrofula and mastocarcinoma and etc. It must have obvious effect upon hemorrhoid, enteritis, constipation and urinary system diseases in experience. |
| Application of pharmacology and goal | Clear away the inflammation symptom in lower abdominal cavity, open and through the lymph nodes of chest and lung, promote the normal circulation of lymph, quicken the pace of treating cancer. |

-continued

No: 32

| | | |
|---|---|---|
| Name of Chinese herbs | Scientific Name/ Another Name | Gleditsia sinensis lam, Gleditsia, Chinese Honeylocust spine, Spina Gleditsiae, spineof Chinese Honeylocust, Gleditsia Spine |
| | Zaojia | |

| | |
|---|---|
| Basis | Page 1144 of Great dictionary of Chinese medicine, Page 480 Volume 4 of China Ben Cao (Shanghai Science and Technology Publishing House, China) |
| Source, Collect Season, Segment of the plant | Sichuan. Reap the flat fruits (falciform) in Autumn when the fruit turns black, then dry under the sun. |
| Processing, Extracting process, Method | (1) Take 4 Kg, cut the edge away, stir-roast with honey. Take its 1 Kg for drying under the sun and grinding into powder. Put another 3 Kg in pot and infuse in water for 3 H, heat and decoct and release the medicinal liquid by 2 times.<br>(2) Heat to evaporate water, mix even with original drug powder when it remains 2.5 KL concentrated liquid.<br>(3) Dry at 45 .<br>(4) Crush and grind the materials throughout 100 mesh sieve, then collect the fine powder for sealing up and storage.<br>Notes: People shall wear respirator as the powder has the urge-sneeze active which can stimulate the nasal's mucosa. |
| Active principle | Contain gledinin, its ligand is gledigenin and leditschia saponin. It also contains ceryl alcohol, nonacosane, heptacosane, stigmasterol, sitosterol, tannin and etc. |

No: 33

| | | |
|---|---|---|
| Name of Chinese herbs | Scientific Name/ Another Name | Angelica biserrate, Angelica, Angelica pubescens Maxim f.biserrata, Doubleteeth pubescent angelica root, Radix Angelicae Pubescentis, Angelica (root), Wild Celery Pubescent Angelica Root, Root of Doubelteeth Pubescent Angelica |
| | Duhuo | |

| | |
|---|---|
| Basis | Page 1703 of Great dictionary of Chinese medicine, Page 877 Volume 5 of China Ben Cao (Shanghai Science and Technology Publishing House, China) |
| Source, Collect Season, Segment of the plant | Sichuan. In October and September, dig out root, get rid of blasted stems and mud, lay open to make partial dry, then pile up in loft, half dry with firewood, arrange each herb straightly, bundle and complete dry with fire. |
| Processing, Extracting process, Method | (1) Take 4 Kg, wash clean, cut open, put in pot and infuse in water for 3H, heat and decoct and release the medicinal liquid by 2 times.<br>(2) Heat to evaporate water, mix even with 1 Kg Fuling powder when it remains 3 KL concentrated liquid.<br>(3) Dry at 65 .<br>(4) Crush and grind the materials throughout 100 mesh sieve, then collect the fine powder for sealing up and storage. |
| Active principle | Contain angelol, angelicone glabralactone, bergapten, osthol, umbelliferone, scopoletin, angelic acid, tiglic acid, palmitic acid, octadecanoic acid, olei acid, linolic acid, phytosterol, glucose and a few volatile oil. |
| Pharmacological action of original record | Remove the abnormal pressure of blood vessel and micrangium and the pathogenic factors caused by obstruction of electrolytic metabolism (rheumatic factors), regulate and increase the temperature on low side, ease pain, relax spasm. Modern pharmacological experiments certify that it can have the anti-arrhythmic action, prolong the time of thrombus forming, ease the pain, relax spasm, relieve inflammation and have the anti-bacterial action. The furanocoumanns composition can inhibit the P from incorporating HeLa cells (cervix cancer cells) and kill and destroy the A's ascitic cancer cells. |
| Application of pharmacology and goal | Regulate the pressure of micrangium, electrolytic metabolism in tissue and temperature on low side. Ancient books record that Duhuo can go deep into tissue and improve the action of unusual symptom. |

No: 34

| | | |
|---|---|---|
| Name of Chinese herbs | Scientific Name/ Another Name | Ephedra sinica stapf, Chinese Ephedra, Ephedra, Herba Ephedrae |
| | Mahuang | |

| | |
|---|---|
| Basis | Page 2221 of Great dictionary of Chinese medicine, Page 349 Volume 2 of China Ben Cao (Shanghai Science and Technology Publishing House, China) |
| Source, Collect Season, Segment of the plant | Shanxi, Nei Meng Gu. Reap the green stems in Autumn, 60% air dry, then dry under the sun, bundle for storage. |
| Processing, Extracting process, Method | (1) Take 4 Kg herb, wash clean, cut into about 30–40 mm segments, put in pot and infuse in water for 3 H, heat and remove the while froth, decoct out the medicinal liquid by 2 times.<br>(2) Heat to evaporate water with small fire, mix even with 1 Kg Fuling powder when it remains 3 KL concentrated liquid.<br>(3) Dry at 45 .<br>(4) Crush and grind the materials throughout 120 mesh sieve, then collect the fine powder for storage. |
| Active principle | Contain ephedrine alkaloids of six kinds such as ephedrine, pseudoephedrine and etc., oxazolones alkaloids. It can be separated out volatile oil compounds of 32 kinds and flavones's compounds. |
| Pharmacological action of original record | Achieve diaphoresis and relieve heat, relieve inflammation, induce diuresis, have the actions of preventing asthma, arresting cough and clearing sputum for respiratory system, excite the central nervous system, increase the transmitting function of nerves and muscles. |
| Application of pharmacology and goal | Excite the central nervous system, increase the transmitting function of nerves and muscles, deepen the drugs into tissue. It's the necessary drug for lung cancer, lymph cancer and osteosarcoma. |

No: 35

| | | |
|---|---|---|
| Name of Chinese herbs | Scientific Name/ Another Name | Cimicifuga foetida L, Cimicifuga Rhizome, shunk bugbane rhizome, Rhizome of Dahurian Bugbane, Rhizome of Shunk Bugbane, Shunk Bugbane |
| | Sheng ma | |

| | |
|---|---|
| Basis | Page 451 of Great dictionary of Chinese medicine, Page 175 Volume 3 of China Ben Cao (Shanghai Science and Technology Publishing House, China) |
| Source, Collect Season, Segment of the plant | Sichuan. Dig out root after the above-ground segment becomes blasted in Autumn, get rid of mud, 80% dry under the sun, fire away the fibrous root, complete dry under the sun, get rid of coat and the remained fibrous root. |
| Processing, Extracting process, Method | (1) Take 6 Kg herb, infuse soft and cut into pieces, put in pot and infuse in water for 3 H, heat and decoct out the medicinal liquid by 2 times.<br>(2) Heat to evaporate water, mix even with 1 Kg Fuling powder when it remains 3 KL concentrated liquid.<br>(3) Dry at 65 .<br>(4) Crush and grind the materials throughout 120 mesh sieve, then collect the fine powder for storage. |
| Active principle | Contain cimicifugine, salicylic acid, tannin resin, caffeicacid, ferulic acid and etc., and other unknown compositions. |
| Pharmacological action of original record | Reduce fever, relieve inflammation, remove the toxin, increase the raising kinetic energy of lymph fluid at lymph vessels, increase the vital capacity (VC), open and through peripheral blood vessels, make the measles virus out of skin. Modem pharmacology explains that Sheng ma can reduce fever, decrease temperature, relieve inflammation, relieve convulsion, nourish liver, relax spasm, and cimicifugins compounds can increase the activity of lymph cells, induce the lymph cells to produce interferon. |

-continued

| Application of pharmacology and goal | Increase the raising kinetic energy of lymph fluid at lymph vessels, increase the activity of lymph cells, induce the lymph cells to produce interferon, produce the special actions at the lymph nodes of enteric aggregate nodules (Peyer's patches) and lymph nodes at thymus. It is not the anti-cancer drug, but the guiding drug for treating intestine cancer, lung cancer, head part cancer and etc. |
|---|---|

(Medicine Preparation)

Mix each ingredient of the above-mentioned concentrated and extracted drug powder (Please read the description of each herb for reference for the method) at specified ratio by mixed machine, add the moderate water, stir to make a few wet, then make tablets with 500 mg/tablet by tablet compression machine, dry at 45 in order to remove the water, put the tablets in glass bottle, seal up and keep at cool and dry places.

(Using Method)

Whether the extensive cancers except liver cancer, pancreas cancer, esophagus cancer, cardia cancer, pylorus cancer and stomach cancer, are diagnosed to be primary cancer, transferring cancer, period of growth or not, whether those patients with such cancers have the resectional, embolizing, chemotherapy and radiotherapy treatment or not, as long as the cancers belong to the extensive and progressive cancers, the drug can be used. Take medicine of 8 tablets (4 mg) with boiled water after 90 minutes of each dinner, three times daily, for children according to age or half dosage.

(Notes)

Patients who have the resectional, embolizing, chemotherapy and radiotherapy treatment, shall take medicine once every over 10 days. During the period of taking medicine, they shall not have the resectional, embolizing, chemotherapy and radiotherapy treatment or take other medicine or healthy food in order not to interfere with treatment. Onion and garlic wine, Chinese prickly ash, capsicum, the five spices (prickly ash, star, aniseed, cinnamon, clove and fennel) and etc., cannot be taken. Burning mosquito repellent incense, spraying insecticide and other toxic materials are forbidden. Don't make strong exercises. Suspend social intercourse and intercommunication.

(Clinical Trials)

1. Goal and Explanation:

Under a certain criterion, test the actual effect and make conclusion by continuous taking the "Chinese medicine for extensive cancers" orally.

Considering the precious life and trials' continuance, when meeting with "Non-cancer disease, accidental symptom", patients can take other drugs temporarily for treatment, but of course the oral medicine shall be taken continuously which doesn't influence the result.

Part of the data and records compiled in this "Practicing Rules for Clinical Trial" are kept in our trial unit. Catamnesis are in catamnesis's data of respective hospitals relatively, and they need to be kept for a certain period according to some regulations of Taiwan.

2. Practice Rules

Medical record remove: those who are not diagnosed by science catamnesis of any third class, well-appointed hospitals should be removed, those who suffer liver cancer, pancreas cancer, esophagus cancer, stomach cancer, cardia cancer should be removed, those whose trial time is less than three courses of treatment (12 days one course) should be removed, considering errors in evaluation of the curative effect.

The effective date is from Mar. 2, 1997 to Oct. 2, 2002, based on the trial/trial day. Those who accord with situation mentioned above, no matter what their cancer species, period class, curative effect, should be fallen under in the practice cases and calculated.

3. Evaluation Standard of Cruative Effect

The standard is divided into three parts: marked effect, effect and inefficacy, according to Curative *Effect Standard of the Cancer therapy by Chinese Drug* released by Central Commission (Ministry of Public Health, China) in 1972.

Marked effect: symptoms vanish basically; reduce cancer focus by more than a half, and other objective examinations are improved obviously. The first class defines symptoms don't recrudesce during more than a half a year, the second class means symptoms don't recrudesce in 2 to 6 months.

Effect: symptoms are improved to some extent, cancer focus keep stable basically for more than a month.

Inefficacy: no improvement for symptoms and objective examinations, or improve in some short time but deteriorate rapidly.

Notes: Besides the above regulations, those who give undefined reply, or are difficult to be evaluated for losing contact are regarded as "Unknown". Those whose symptoms and focus deteriorate or are returned to original situation in the trial after improving to some extent or keeping stable for more than a month, are defined inefficacy.

(Efficiency and Statistics)

Out of the 83 cases accord with the trial rule. As the result, 26 cases showed marked effect, 42 cases showed effect, total 68 cases are effect, accounting for 82%; inefficacy is 12 cases, unknown is 3 cases, total 15 cases is inefficacy, accounting for 18%. The number and efficiency of cancer species are described in the following chart.

| Cancer | Cases Number | Marked effect | Effect | Inefficacy | Unknown |
|---|---|---|---|---|---|
| Lung | 17 | 3 | 11 | 2 | 1 |
| Lymph | 11 | 3 | 8 | 0 | 0 |
| Oral cavity, nasopharynx, throat, tongue, hypothyroid, etc | 13 | 4 | 6 | 3 | 0 |
| Breast | 11 | 6 | 3 | 1 | 1 |
| Uterus appendages | 10 | 2 | 7 | 0 | 1 |
| Bone | 5 | 2 | 0 | 3 | 0 |
| Bladder, prostate | 6 | 2 | 3 | 1 | 0 |
| Intestine | 5 | 1 | 2 | 2 | 0 |
| Brain | 2 | 1 | 1 | 0 | 0 |
| Blood | 1 | 0 | 1 | 0 | 0 |
| Kidney | 1 | 1 | 0 | 0 | 0 |
| Total | 83 | 26 | 42 | 12 | 3 |
| Rate | 1 | 0.8192 | | 0.1807 | |

Gender and age: the male total 35, the female total 48 (uterus cancer and breast cancer patients included), the eldest born in 1919(aged 83), the youngest born in 1985 (aged 17), the average age 54 (calculated in 2002). Diagnosis proof: the persons diagnosed by the first-class teaching hospitals total 17, by second-class regional hospitals total 58, by third-class local hospitals total 8.

After diagnosis, those in the trial from lower third-class hospitals or after finding their own drugs ineffective total 73, direct participants total 10, sum to 83.

(Statistics of the Cancer Species Transfer)

Explanation:

1. The objective of the statistics is to prove new ideas of type mechanism in this application by analyzing the characteristics of cancer species, especially upper, lower cancers' transfer and the influence of actinotheraphy and chemotherapy treatment on the characteristics, according to actual cancer patients information.

2. Mark the cancer category in this clinical trial. Based on the data of 83 cases, looking for the "primary cancers" will do benefit for the tracing of the transferring trends.

3. Upper center: means the above parts of diaphragm, including head, mouth, the above part of chest. There are 51 patients of primary upper center cancer. Lower center: means the underside parts of pancreas, liver and stomach, including the underside part of nephridium and bones. There are 32 patients of primary lower center cancer. Radio-: means the radiotherapy. Chemo-: means the therapy of dripping and transfusing chemical drugs. There are 31 patients who have the radiotherapy and chemotherapy treatment in the 83 cases, while other 52 patients don't have such treatment.

4. Transfer down: means that the primary upper center cancers are transferred down or to be lower center. Transfer up: means that the cancers are transferred up, or to be upper center. Level transfer: means that those primary upper center or lower center cancers are transferred breadthwise to the neighboring organs. No transfer: means that cancers work at the primary organs, or can be regenerated and then diffused in the primary organs after the resectional, radiotherapy and chemotherapy treatment.

Statistical Chart:

| Upper center cancer: 51 cases | Transfer down | Level transfer | No transfer |
|---|---|---|---|
| Radiotherapy and chemotherapy: 21 cases | 10 cases | 5 cases | 6 cases |
| No radiotherapy and chemotherapy: 30 cases | 1 case | 5 cases | 24 cases |
| Total: 51 cases | 11 cases | 10 cases | 30 cases |

| Lower center cancer: 32 cases | Transfer up | Level transfer | No transfer |
|---|---|---|---|
| Radiotherapy and chemotherapy: 10 cases | 5 cases | 3 cases | 2 cases |
| No radiotherapy and chemotherapy: 22 cases | 6 case | 3 cases | 13 cases |
| Total: 32 cases | 11 cases | 6 cases | 15 cases |

1. Comparison of the Upper/Lower Center Cancer Transferring Down/Up:

A. Mixed (whether have the radiotherapy and chemotherapy treatment):

The upper center cancer transferring down: 11/51=0.21, the lower center cancer transferring up: 11/32=0.34

B. No radiotherapy and chemotherapy:

The upper center cancer transferring down: 1/30=0.033, the lower center cancer transferring up: 6/22=0.272

0.21<0.34, 0.03<0.27

Upper center cancer transferring down<lower center cancer transferring up. Under the standings of no radiotherapy and chemotherapy treatment, the upper center cancer transferring down=⅛ the lower center cancer transferring up.

2. Comparison of the Transfer (Including Level Transfer) of Upper/Lower Center Cancer A. Mixed (whether have the radiotherapy and chemotherapy treatment):

Transfer of the upper center cancer: 11/51+10/51=21/51=0.412

Transfer of the lower center cancer: 11/32+6/32=17/32=0.531

B. No radiotherapy and chemotherapy:

Transfer of the upper center cancer: 1/30+5/30=6/30=0.200

Transfer of the lower center cancer: 6/22+3/22=9/22=0.409

0.412<0.53, 0.20<0.41

The transfer of upper center cancer is a little less than that of lower center cancer. Under the standings of no radiotherapy and chemotherapy, the transfer of upper center cancer=½ the transfer of lower center cancer.

3. Comparison of Transfer Up, Transfer Down and Transfer Under the Standings of Radiotherapy and Chemotherapy or no Radiotherapy and Chemotherapy:

A. The upper center cancer transferring down and the lower center cancer transferring up:

The upper center cancer transferring down with the radiotherapy and chemotherapy treatment: 10/21=0.476

The upper center cancer transferring down without the radiotherapy and chemotherapy treatment:

1/30=0.033

The lower center cancer transferring up with the radiotherapy and chemotherapy treatment:

5/10=0.5

The lower center cancer transferring up without the radiotherapy and chemotherapy treatment:

6/22=0.272

B. Transfer of the upper center cancer (including level transfer) and transfer of the lower center cancer:

Transfer of the upper center cancer with the radiotherapy and chemotherapy treatment:

10/21+5/21=15/21=0.71

Transfer of the upper center cancer without the radiotherapy and chemotherapy treatment:

1/30+5/30=6/30=0.20

Transfer of the lower center cancer with the radiotherapy and chemotherapy treatment:

5/10+3/10=8/10=0.80

Transfer of the lower center cancer without the radiotherapy and chemotherapy treatment:

6/22+3/22=9/22=0.409

Proportion of transfer of upper center cancer with/without the radiotherapy and chemotherapy treatment:

Transfer down-0.476>0.033=14.5

Transfer-0.710>0.20=3.5

Proportion of transfer of lower center cancer with/without the radiotherapy and chemotherapy treatment:

Transfer up-0.50>0.27=1.8

Transfer-0.80>0.41=1.9

Conclusion:

1. As shown in the statistic of 1, the upper center cancer transferring down 0.21<the lower center cancer transferring up 0.34. Under the standings without the radiotherapy and chemotherapy treatment, the upper center cancer transferring down 0.03 is just ⅛ of the lower center cancer transferring up.

2. As shown in the statistic of 2, the transfer of the upper center cancer 0.412 is a little less than that of the lower center cancer 0.53. Under the standings without the radiotherapy and chemotherapy treatment, the transfer of upper center cancer is ½ of that of lower center cancer.

3. As shown in the statistic of 3, the upper heat cancer transferring down with the radiotherapy and chemotherapy treatment is 14.5 times of that without the radiotherapy and chemotherapy treatment, while the multiple of transfer is 3.5. Therefore, the treatment of radiotherapy and chemotherapy for the upper center cancer has the obvious disadvantages of urging cancerous cells transferring down or transferring. The lower center cancer transferring up with the radiotherapy and chemotherapy is 1.8 times of that without the radiotherapy and chemotherapy, while transfer is 1.9 times. The seriousness of the lower center cancer is much lower than that of the upper center cancer as the lower center cancer has the instinct of transferring up.

4. In summary, we conclude as follows: A. The ability of transferring down for the upper center cancer is very low, lower than that of transferring up and level transfer. B. The radiotherapy and chemotherapy treatment for the upper center cancer doesn't do benefit for patients. The transfer ability after the radiotherapy and chemotherapy treatment can be raised 4.5 times, while the ability of transferring down can be raised 15.5 times. C. Under the standings without the radiotherapy and chemotherapy treatment, the lower center cancer transferring up is 8 times of the upper center cancer transferring down; while the influence of transferring up and transfer is a little less after the radiotherapy and chemotherapy treatment. D. As far as the circumstances are concerned, there must be some deficiencies for data. Hope the large-scale concerning research institutions may make statistics by the way and find out more authentic results.

(Standard Cases of Clinical Trials)

In this patent book, we only give 9 cases for brief explanation, while read the attachment 1 for other 65 cases and details.

(1) No.1 Miss Hong, Lung Cancer, Born in 1985 (17 Years Old)

In December 2000, she was found to have lower bone cancer for right knee cap diagnosed by a second-class hospital in Tainan. On December 26, her right lower limb was excised and she was taken the whole course chemotherapy treatment.

In August 2001, she was found to have urgent sound of cough and difficulty in breathing. After examination, the cancerous cells were found to transfer to lung. Then she got an operation, but as far as the ultra-large cancer volume was concerned, the operation couldn't be continued.

On Sep. 14, 2001, she took part in this trial. Up to October 26 this year, the main symptom was improved obviously and no pain could be touched. After 4 courses of treatment, the main symptom completely disappeared, then end medicine. On Feb. 9, 2002, the place that the right foot cancer was excided became swollen and inflammation. She took this medicine and other drugs, recovered fully in two courses of treatment.

(2) No.9 Ms. Zhan, Lung Cancer, Born in 1942 (60 Years Old)

In 1995, her breast cancer was excided. In November 1998, the cancer was transferred to right clavicle upper lymph cancer (lymphomas) diagnosed by Chang Hua second-class religion hospital. She then accepted the radiotherapy and chemotherapy treatment. In April 2000, the cancer was transferred to left oxter. Again excided the cancer by the original hospital and accept the chemotherapy treatment. In January 2001, she was found to get lung cancer after another examination.

On Feb. 1, 2001, she took part in this trial. Symptom: A. rapid respiration, oppressing sensation in chest, pain in chest when coughing. B. abdominal-lumbar swelling sensation, pain when pressing the lower abdomen. C. anaphylactic reaction for right arm because of the radiotherapy and chemotherapy treatment, lymph swelling, cutaneous edema. D. edema of the legs.

On Mar. 23, 2001, the main symptom got better and was improved obviously. Examination found out that the cancer swollen mass was not formed and enlarged. She was recovered fully after the whole treatment except that the cutaneous edema of right arm was improved a few.

(3) No.18, Ms. Chen, Lymph Cancer, Born in 1951 (51 Years Old)

In March 1999, she was diagnosed to have cervix cancer by a second-class specialty hospital in Tainan. On March 17, her uterus and ovary were excided and she accepted 28 times of radio-electrotherapy treatment and 5-week chemotherapy treatment continuously (once a week), but with no more improvement. Then tried cocktail therapy in vain. After 15 days of chemotherapy treatment, she was found to have swelling in foot, continuous pain in lumbar bone of right upper limb. Then she was transferred to a second-class hospital in Kaohsiung for examination. It was certified that the cancer was transferred to lymph and marrow, and the right hand was disabled. She was moved to peaceful ward and used anesthetic for alleviating pain as the final arrangement.

On Aug. 10, 2000, she took part in this trial. Main symptoms: A. upper lympth cancer's lump in left clavicle is approximately 5 CM. B. disability of the right upper extremity. C. lumbar-back continuous ache, use anesthetic for alleviating pain. D. mild pain at that resectional aterus-ovary place. E. swelling in left foot after chemo-radiotherapy treatment. Others: 5-spoon food each dinner, very weak, difficulty in walking, constipation and dry stool, scanty urine.

On Aug. 22, 2000, the pain at the lumbar-back, right scapula was obviously improved in half course of treatment, she was unnecessary to use anesthetic, and she was comfortable with lower abdomen and her bowels was relieved. On September 6, the main symptoms were again improved, no pain, the upper lymph cancer's lump in left clavicle was half relieved and her right hand could move. Later the cancer's lump became serious and her right arm again ached which was resulted from the direct-sales healthy food taken by mistake. Until October 17 of taking this medicine, the lump disappeared, her right arm recovered and the continuous ache in her lumbar-back completely disappeared. On November 5, she was just like other healthy person except that the upper cancer's lump in left clavicle only had 0.2 CM. No recrudescence occurred until June 2002.

(4) No. 23, Ms. Guo, Lymph Cancer, Born in 1946 (56 Years Old)

On October 1999, she was diagnosed to have bladder cancer by a first-class teaching hospital in the south and got the operation. On May 2000, she was found out that the cancer was transferred to rectum cancer by tracing examination. She couldn't be operated for some certain reasons and therefore accepted 5 times of therapy of dripping and transfusion of chemical drug. Soon, her left clavicle was found lymph cancer's lump approximately 3.5 CM, then she was diagnosed to have lymph cancer. Then she was inserted into renal catheter, carried urine-bag. The original hospital ended its treatment.

On Mar. 10 2001, she took part in this trial. Main symptoms: A. the upper lymph cancer's lump in left clavicle was approximately 3.5 CM. B. gripping pain in lower abdomen, unable to sustain the pain of the lumbar-buttocks. C. defecation was hurried first then defecating, difficultly in defecation. Others: bad appetite, weak and etc.

On Mar. 21, 2001, the symptoms of B and C were greatly improved. On March 28, the lymph cancer's lump of A was slowly removed but she was aching the pain of the lumbar-buttocks. On April 8, the main symptoms were again improved. On May 9, the lymph cancer's lump occurred again resulted from the direct-sales healthy food. On May 16, the symptoms were continuously improved and maintained for over 30 days.

(5) No. 29, Mr. Wen, Oral Cavity Cancer, Born in 1924 (78 Years Old)

Have diabetes. On December 16, 1998, he was diagnosed to have oral cavity cancer by a second-class hospital. The symptoms were continuously deteriorated after the treatment by original hospital and taking many drugs.

On Oct. 17, 1999, he took part in this trial. Main symptoms: A. ulcer of oral cavity near pharynx, cancer's little lump appeared among the left cheek and gum, swelling and hard in submandibular gland, difficulty in opening. B. stuffiness in the abdomen. C. cough at night. Others: fatigue and weakness, feeling limp, difficulty in walking.

On Oct. 31, 1999, ulcer symptom was improved, the swelling of submandibular gland disappeared, and the symptoms of stuffiness in chest and abdomen and cough were reduced. On November 17, the main symptoms were again improved, the consciousness and physical energy got better and blood sugar before dinner was normal (not take other Hypoglycemic Drugs). On December 2, original cancer pain disappeared so that he can help family members feed pigs and do other work. Till April 2002, the symptom of original cancer never occurred.

(6), No.42, Ms. Qiu, Breast Cancer, Born in 1954 (48 Years Old)

She was diagnosed to have breast cancer by a first-class hospital in the south at first, and accepted unknown therapy at its private clinique. Because the state of illness wasn't improved, she was transferred to a second-class army hospital for confirmation and accepted medicine therapy. Hospital suggested chemotherapy treatment in vain. On Apr. 25, 2000, she took part in this trial. Main symptoms: A. hard cancer mass and lump appeared in the intra- and extra-side of right breast. Nipple had mild ulcer. Others: often have constipation and borborygmus.

On May 9 2000, in the first course of treatment, cancer mass was softened slowly. As far as the permeability of drugs was concerned, she could accept its throb of pain. On May 24, cancer mass got soft, small and a few throb of pain. On June 9, breast cancer mass was relieved and removed, nipple was recovered, decrustation.

(7) No.54, Ms. Chen, Ovary Cancer, Born in 1962 (40 Years Old)

She was old patient of trial unit. She was diagnosed to have left ovary cancer by a second-class hospital in ovary cancer and accepted this trial directly on Sep. 18, 1999. Main symptoms: A. accidental swelling and pain in lower abdomen. B. stuffiness in stomach. C. the private parts have yellow mixed secretion. Others: common constipation, frequency of urination.

On Sep. 18, 1999, she started to accept this trial, but she couldn't continue taking this medicine because of family misfortune. Till May 31, 2000, she only took medicine of 5 courses of treatment and the symptoms disappeared basically. On May 5, 2000, she took CT in the original diagnosed hospital and was found that left ovary cancer was removed completely, and no transfer and diffusion were found. In May 2002, she kept healthy by examination.

(8) No.63, Mr. Wen, Bone Cancer, Born in 1952 (45 Years Old)

In December 1996, he was examined and confirmed that he got Multiple Myeloma which had already diffused up to 3 points and meanwhile got the complication of diabetes. He took 15-times radio-electrotherapy treatment, but the status continuously deteriorated.

On Jun. 3, 1997, he took part in this trial. Main symptoms: A. muscle-tendon of lower limbs disappeared, unbearable pain in the leg-buttocks, swelling of foot tibia, atrophic debility of the foot, difficulty in lifting up foot. B. cough, multiple phlegm in the pharynx. C. stuffiness and malaise in the abdomen. Others: thirsty, frequency and oliguria with reddish urine, accidental constipation, appetite abnormity, appetite increased.

On Jun. 15, 1997, he could walk in a course of treatment, pain was relieved to be bearable, swelling of foot tibia was removed, but uncomfortable in the abdomen where accepted radio-electrotherapy. On July 11, he could move normally and cough was relieved. On August 3, cancerous cells were stable, AFP normal and urine glucose AC200 tested by original hospital. On August 15, red and white blood cells were approximately normal. On August 28, muscle in lower limbs regrown, urine glucose normal. On October 9, he was examined by the original hospital and found that cancerous cells were controlled and hematocytes were normal.

(9) No.68, Mr. Huang, Bladder Cancer, Born in 1954 (46)

In December 1999, he was diagnosed to have colorectal cancer/large-intestine cancer. The cancer was excided and he was set up artificial anus. In March 2000, he was traced and examined and found that the cancer was transferred to bladder. Then opened and scrapped and removed it by operation, but found the cancerous cells' regeneration soon.

On Jun. 22, 2000, he took part in this trial. Main symptoms: A. part bladder had the irritating sensation, frequency and oliguria with urine. B. side ache in the right lower abdomen. Others: inappetence, fatigue, weakness and other accessory symptoms. On July 4, symptom A disappeared, symptom B was improved, but he had sensation of a throb of pain when coughing. On July 17, symptom A and B were all disappeared.

After 600 days, on Mar. 20, 2002, he came for examination and was found that all colorectal cancer and bladder cancer had not been recrudescent during the period. Since August 2000, he can work and live normally.

What is claimed is:

1. A composition of herbs for treating cancer comprising effective amounts of Pilose asiabell root, Astragalus root, Coix seed, Eupatorium, Tangerine peel, Justicia, Prunella spike, Serissa serissoides, Capejasmine fruit, Forsythia fruit, Red peony root, Rhubarb, Blister beetle, Oldenlandia, Polygonum perfoliatum, Subprostrate sophora root, Shrubalthea bark, Rhizome of arisaema, Chinese Lobelia, Ampelopsis, Globethistle, Pyrrosia leaf, Frankincense, Myrrh, Paris chinensis franch, Patrinia, Dahurian angelica root, Belamcanda rhizome, Dandelion herb, Lemmaphyllum microphyllum, Gleditsia spine, Pubescent angelica root, Chinese Ephedra, and Cimicifuga rhizome.

2. The composition of claim 1 further comprising Fuling.

* * * * *